(12) United States Patent
Divita et al.

(10) Patent No.: US 10,111,965 B2
(45) Date of Patent: *Oct. 30, 2018

(54) CELL PENETRATING PEPTIDES FOR INTRACELLULAR DELIVERY OF MOLECULES

(71) Applicant: AADIGEN LLC, Pacific Palisades, CA (US)

(72) Inventors: Gilles Divita, Saint-Andre-de-Sangonis (FR); Sebastien Deshayes, Montpellier (FR); Karidia Konate, Montpellier (FR); May Catherine Morris, Mauguio (FR)

(73) Assignee: Aadigen, LLC, Pacific Palisades, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/428,864

(22) Filed: Feb. 9, 2017

(65) Prior Publication Data

US 2017/0258928 A1    Sep. 14, 2017

Related U.S. Application Data

(63) Continuation of application No. 14/433,570, filed as application No. PCT/EP2013/070676 on Oct. 4, 2013, now Pat. No. 9,579,395.

(30) Foreign Application Priority Data

Oct. 4, 2012  (WO) .................. PCT/IB2012/055343

(51) Int. Cl.
| | |
|---|---|
| *A61K 47/42* | (2017.01) |
| *A61K 47/62* | (2017.01) |
| *A61K 47/64* | (2017.01) |
| *A61K 9/00* | (2006.01) |
| *A61K 49/00* | (2006.01) |
| *A61K 9/51* | (2006.01) |
| *A61K 31/704* | (2006.01) |
| *A61K 31/7088* | (2006.01) |
| *A61K 39/395* | (2006.01) |
| *A61K 38/02* | (2006.01) |
| *C07K 7/08* | (2006.01) |
| *A61K 47/60* | (2017.01) |

(52) U.S. Cl.
CPC ............ *A61K 47/64* (2017.08); *A61K 9/0019* (2013.01); *A61K 9/5169* (2013.01); *A61K 9/5192* (2013.01); *A61K 31/704* (2013.01); *A61K 31/7088* (2013.01); *A61K 38/02* (2013.01); *A61K 39/395* (2013.01); *A61K 47/42* (2013.01); *A61K 47/60* (2017.08); *A61K 47/645* (2017.08); *A61K 47/6455* (2017.08); *A61K 49/0056* (2013.01); *A61K 49/0093* (2013.01); *C07K 7/08* (2013.01)

(58) Field of Classification Search
CPC .. A61K 38/10; A61K 47/42; A61K 47/48246; A61K 47/48315; A61K 47/4833; A61K 47/64; A61K 47/645; A61K 47/6455; C07K 7/08
See application file for complete search history.

(56) References Cited

U.S. PATENT DOCUMENTS

| | | | |
|---|---|---|---|
| 7,514,530 B2 | 4/2009 | Divita et al. | |
| 9,376,468 B2 | 6/2016 | Divita et al. | |
| 9,579,395 B2* | 2/2017 | Divita .................. | A61K 9/0019 |
| 9,598,465 B2 | 3/2017 | Divita et al. | |
| 9,834,581 B2 | 12/2017 | Divita et al. | |
| 2016/0145299 A1 | 5/2016 | Divita et al. | |
| 2017/0081661 A1 | 3/2017 | Divita et al. | |

FOREIGN PATENT DOCUMENTS

| | | |
|---|---|---|
| EP | 1 795 539 A1 | 6/2005 |
| WO | WO-2007/069090 A2 | 6/2007 |
| WO | WO-2007/069090 A3 | 6/2007 |

OTHER PUBLICATIONS

Barre-Sinoussi, F. et al. (May 20, 1983) "Isolation of a T-Lymphotropic Retrovirus from a Patient at Risk for Acquired Immune Deficiency Syndrome (AIDS)," *Science* 220(4599):868-871.
Crombez, L. et al. (2009, e-pub. May 29, 2009). "Targeting Cyclin B1 Through Peptide-Based Delivery of siRNA Prevents Tumor Growth," *Nucleic Acid Research* 37(14):4559-4569.
Crombez, L. et al. (Jan. 2009). "A New Potent Secondary Amphipathic Cell-Penetrating Peptide for siRNA Delivery Into Mammalian Cells," *Mol. Ther.* 17(1):95-103.
Deshayes, S. et al. (2005). "Cell-penetrating Peptides: Tools for Intracellular Delivery of Therapeutics," *Cell Mol Life Sci.* 62:1839-1849.
Deshayes, S. et al. (2008, e-pub. Oct. 25, 2007). "Delivery of Proteins and Nucleic Acids Using a Non-Covalent Peptide-Based Strategy," *Adv. Drug Deliv. Rev.* 60:537-547.
Glover, D.J. et al. (Apr. 2005, e-pub. Mar. 10, 2005). "Towards Safe, Non-Viral Therapeutic Gene Expression in Humans," *Nat. Rev. Genet.* 6:299-310.
Heitz, F. et al. (2009). "Themed Section: Vector Design and Drug Delivery Review. Twenty Years of Cell-Penetrating Peptides: From Molecular Mechanisms to Therapeutics," *British Journal of Pharmacology* 157:195-206.
Kurzawa, L. et al. (2010, e-pub. Feb. 25, 2010). "PEP and CADY-mediated 1-23 delivery of fluorescent peptides and proteins into living cells," *Biochimica Et Biophysica Acta* 1798(12):2274-2285.

(Continued)

*Primary Examiner* — Jeffrey E. Russel
(74) *Attorney, Agent, or Firm* — Morrison & Foerster LLP

(57) ABSTRACT

A cell-penetrating peptide characterized in that it comprises an amino acid sequence $X_3X_4X_1X_2X_5X_4X_1X_2X_6X_7X_1X_8X_9X_{10}X_{11}X_{12}X_{13}$ (SEQ ID No: 11), wherein $X_1$ is F or W, $X_2$ is F, W or Y, $X_3$ is beta-A or S, $X_4$ is K, R or L, $X_5$ is E, R or S, $X_6$ is R. T or S, $X_7$ is E, R or S, $X_8$ is none, F or W, $X_9$ is P or R, $X_{10}$ is R or L, $X_{11}$ is K, W or R, $X_{12}$ is R or F and $X_{13}$ is R or K.

20 Claims, 14 Drawing Sheets

Specification includes a Sequence Listing.

(56) References Cited

OTHER PUBLICATIONS

Mery, J. et al. (Jul./Aug. 1992). "Disulfide Bond as Peptide-Resin Linkage in Boc-Bzl SPPS, for Potential Biochemical Applications," *Pept Res.* 5(4):233-240.
Morris, M.C. et al. (1997). "A New Peptide Vector for Efficient Delivery of Oligonucleotides Into Mammalian Cells," *Nucleic Acids Res.* 25(14):2730-2736.
Morris, M.C. et al. (Dec. 2001). "A Peptide Carrier for the Delivery of Biologically Active Proteins Into Mammalian Cells," *Nat. Biotechnol.* 19:1173-1176.
Morris et al. (2007, e-pub. Mar. 5, 2007) "A Non-Covalent Peptide-Based Carrier for in vivo Delivery of DNA Mimics," *Nucleic Acids Research* 35(7):e49.
Roisin, A. et al. (Mar. 5, 2004—e-pub. Dec. 10, 2003) "Inhibition of HIV-1 Replication by Cell-penetrating Peptides Binding Rev." *J. Biol. Chem.* 279(10):9208-9214.
Verdine, G.L. et al. (2012). "Stapled peptides for Intracellular Drug Targets," Chapter 1 in *Methods in Enzymology,* 503:3-33.
Whitehead, K.A. et al. (Feb. 2009). "Knocking Down Barriers: Advances in siRNA Delivery," *Nat Rev Drug Discov.* 8:129-138.
International Search Report issued in corresponding International Patent Application No. PCT/EP2013/070676 dated Dec. 12, 2013.
U.S. Appl. No. 15/539,619, filed Dec. 23, 2015, by Divita et al.
U.S. Appl. No. 15/463,994, filed Mar. 20, 2017, by Divita et al.
U.S. Appl. No. 15/802,402, filed Nov. 2, 2017, by Divita et al.

\* cited by examiner

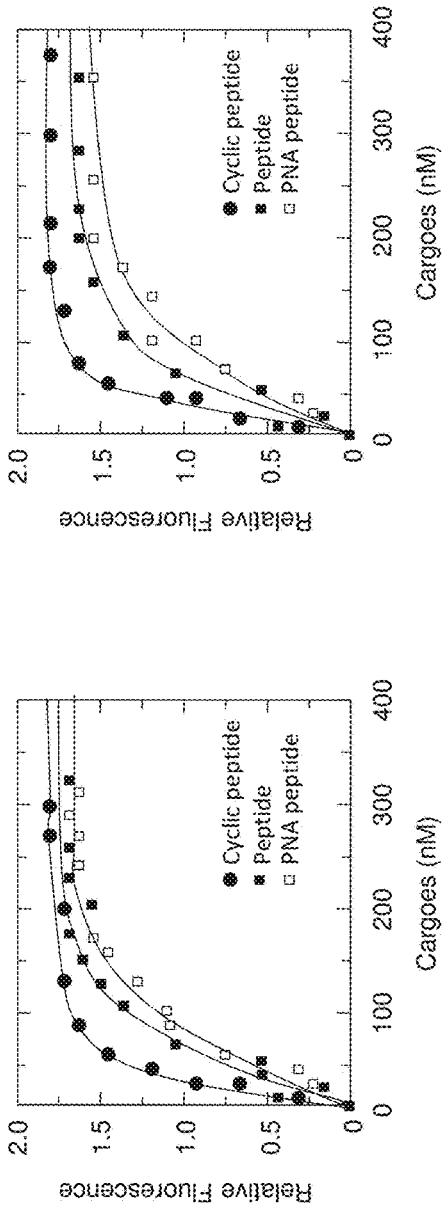
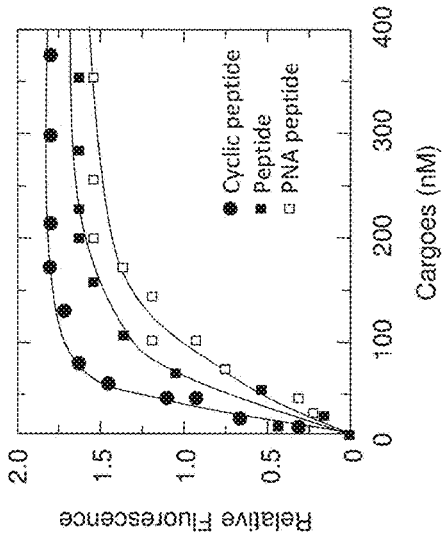
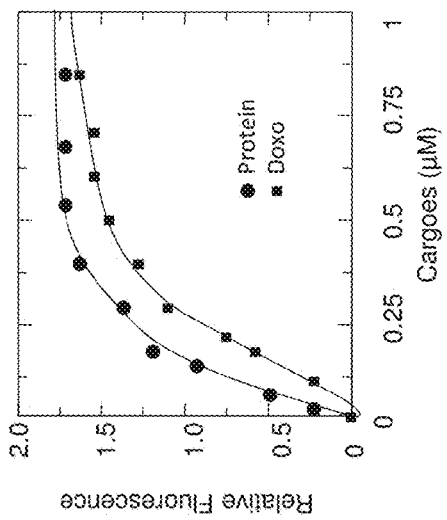
FIG. 1A  VEPEP-3a
FIG. 1B  VEPEP-3c
FIG. 1C  VEPEP-3g

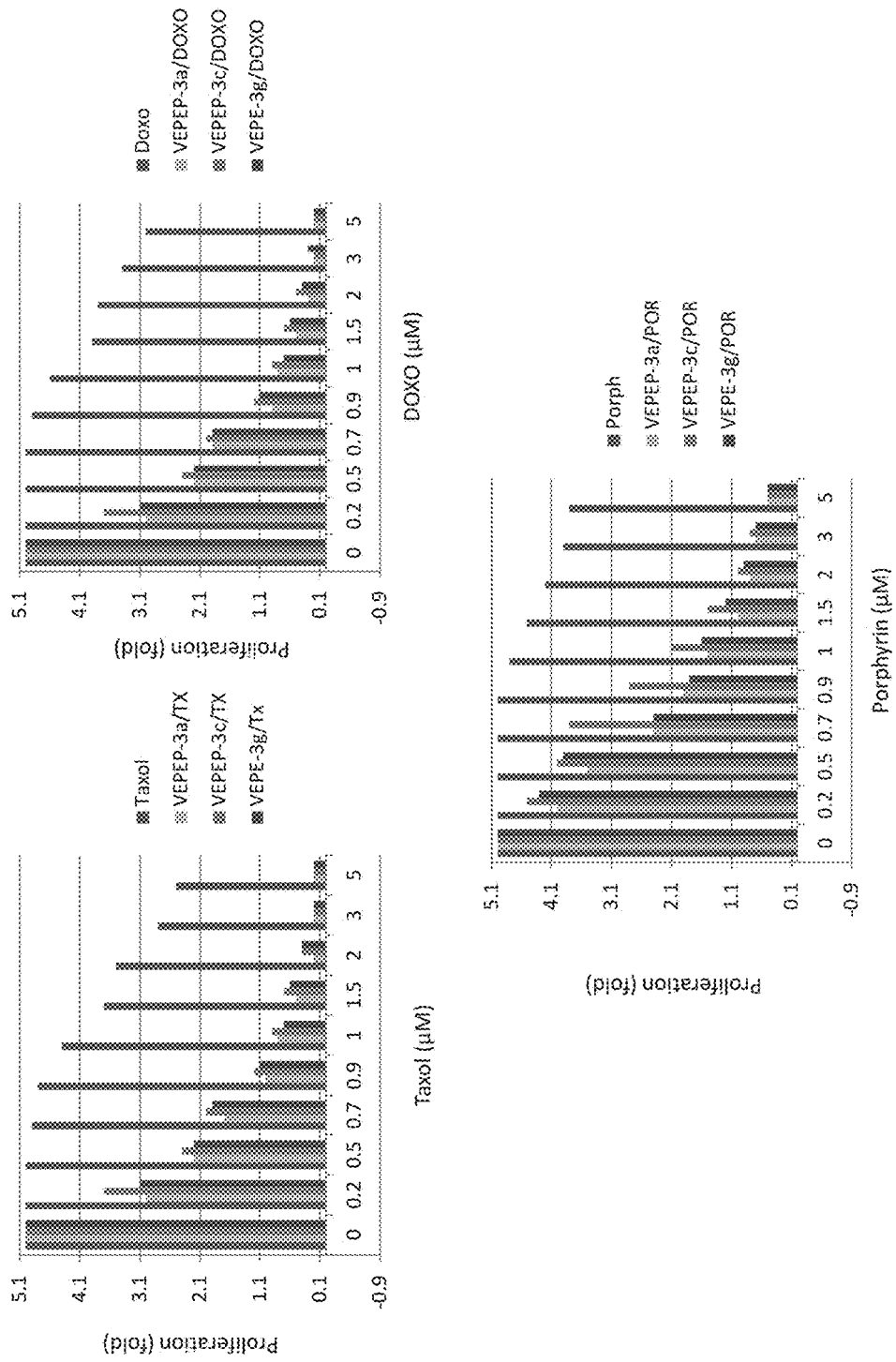

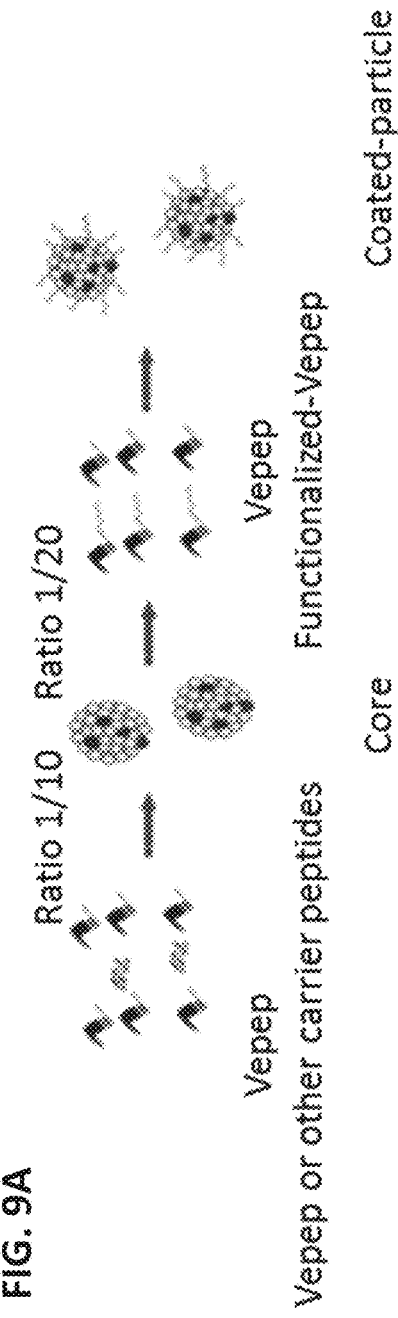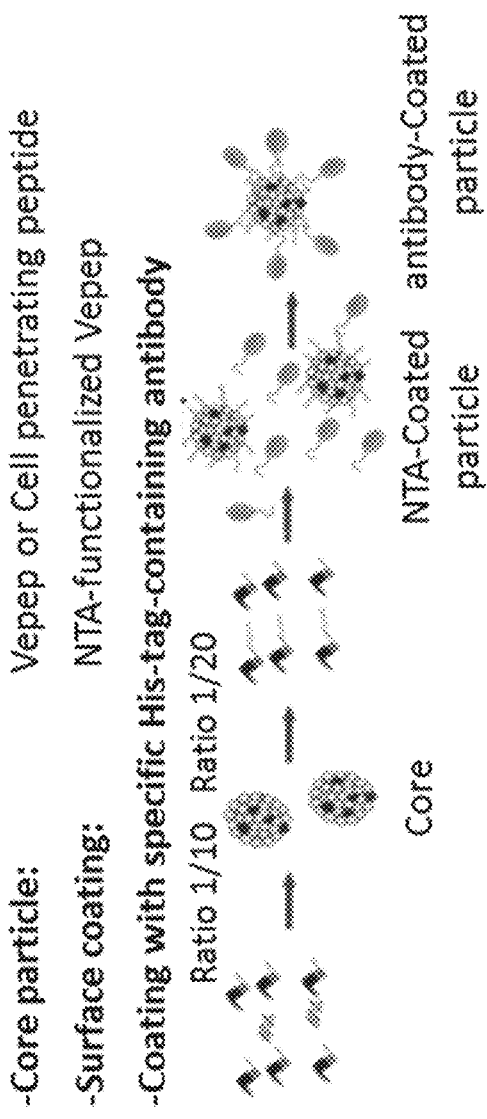

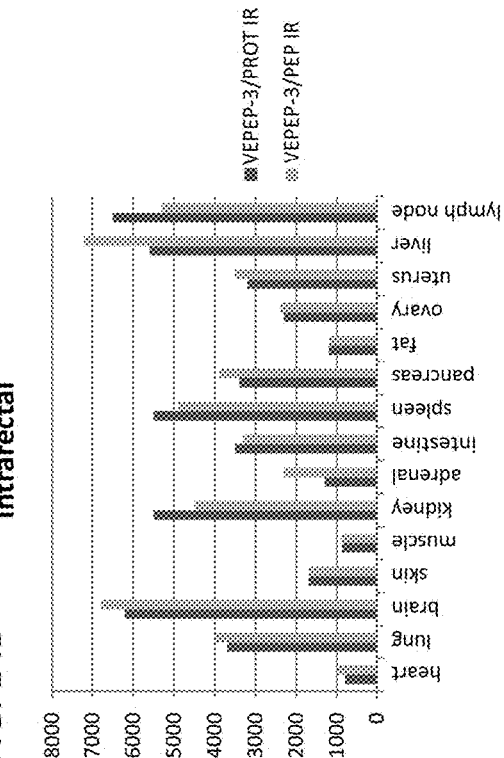
FIG. 14A Intravenous
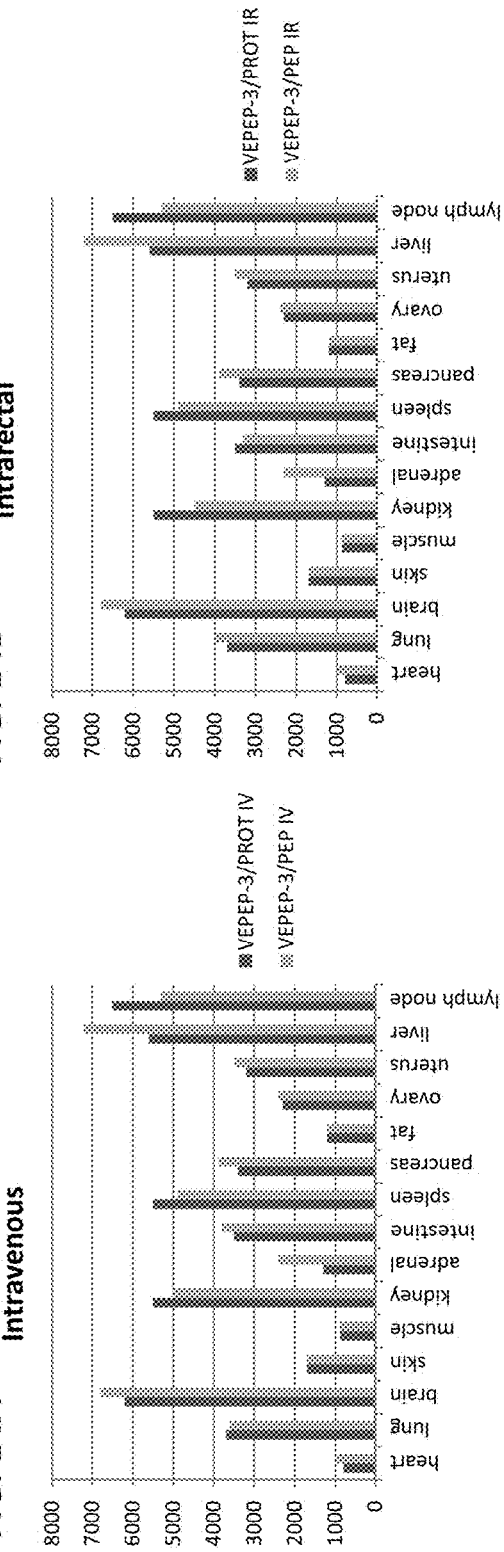
FIG. 14B Intrarectal
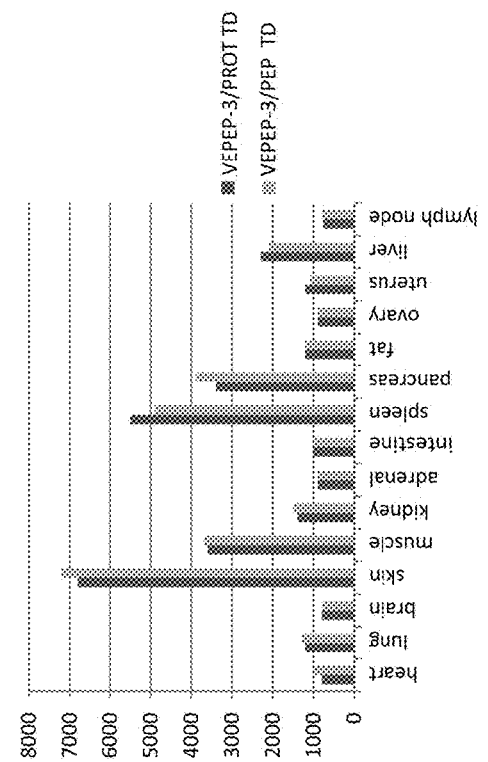
FIG. 14C Intranasal
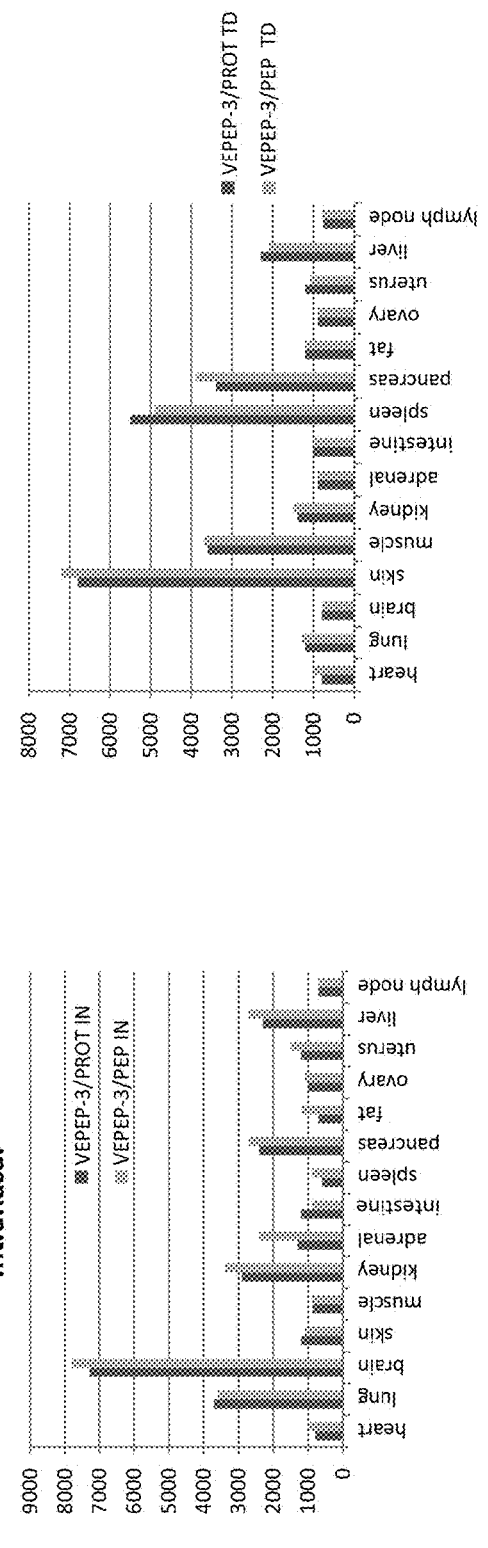
FIG. 14D Transdermal

SEQUENCE LISTING

```
<160> NUMBER OF SEQ ID NOS: 52

<210> SEQ ID NO 1
<211> LENGTH: 16
<212> TYPE: PRT
<213> ORGANISM: Artificial Sequence
<220> FEATURE:
<223> OTHER INFORMATION: synthesized peptide VEPEP-3a
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 1

Xaa Lys Trp Phe Glu Arg Trp Phe Arg Glu Trp Pro Arg Lys Arg Arg
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthesized peptide VEPEP-3b
```

```
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 2

Xaa Lys Trp Trp Glu Arg Trp Trp Arg Glu Trp Pro Arg Lys Arg Lys
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthesized peptide VEPEP-3c
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 3

Xaa Arg Trp Trp Glu Lys Trp Trp Thr Arg Trp Pro Arg Lys Arg Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthesized peptide VEPEP-3d
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 4

Xaa Arg Trp Tyr Glu Lys Trp Tyr Thr Glu Phe Pro Arg Arg Arg Arg
1               5                   10                  15

<210> SEQ ID NO 5
<211> LENGTH: 17
<212> TYPE: PRT
<213> ORGANISM: Artificial Sequence
<220> FEATURE:
<223> OTHER INFORMATION: synthesized peptide VEPEP-3e
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 5

Xaa Arg Trp Trp Arg Leu Trp Trp Arg Ser Trp Phe Arg Leu Trp Arg
1               5                   10                  15

Arg

<210> SEQ ID NO 6
<211> LENGTH: 17
<212> TYPE: PRT
<213> ORGANISM: Artificial Sequence
<220> FEATURE:
<223> OTHER INFORMATION: synthesized peptide VEPEP-3f
<220> FEATURE:
<221> NAME/KEY: MISC_FEATURE
<222> LOCATION: (1)..(1)
<223> OTHER INFORMATION: Xaa = beta-Alanine or Serine
```

-continued

```
<400> SEQUENCE: 6

Xaa Leu Trp Trp Arg Arg Trp Trp Ser Arg Trp Trp Pro Arg Trp Arg
1               5                   10                  15

Arg

<210> SEQ ID NO 7
<211> LENGTH: 17
<212> TYPE: PRT
<213> ORGANISM: Artificial Sequence
<220> FEATURE:
<223> OTHER INFORMATION: synthesized peptide VEPEP-3g
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 7

Xaa Leu Trp Trp Ser Arg Trp Trp Arg Ser Trp Phe Arg Leu Trp Phe
1               5                   10                  15

Arg

<210> SEQ ID NO 8
<211> LENGTH: 17
<212> TYPE: PRT
<213> ORGANISM: Artificial Sequence
<220> FEATURE:
<223> OTHER INFORMATION: synthesized peptide VEPEP-3h
<220> FEATURE:
<221> NAME/KEY: MISC_FEATURE
<222> LOCATION: (1)..(1)
<223> OTHER INFORMATION: Xaa = beta-Alanine or Serine

<400> SEQUENCE: 8

Xaa Lys Phe Trp Ser Arg Phe Trp Arg Ser Trp Phe Arg Leu Trp Arg
1               5                   10                  15

Arg

<210> SEQ ID NO 9
<211> LENGTH: 17
<212> TYPE: PRT
<213> ORGANISM: Artificial Sequence
<220> FEATURE:
<223> OTHER INFORMATION: synthesized peptide VEPEP-3bstapl
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (3)..(3)
<223> OTHER INFORMATION: Xaa = non-natural amino acid used for the
      binding of a hydrocarbon staple
<220> FEATURE:
<221> NAME/KEY: MISC_FEATURE
<222> LOCATION: (11)..(11)
<223> OTHER INFORMATION: Xaa = non-natural amino acid used for the
      binding of a hydrocarbon staple

<400> SEQUENCE: 9

Xaa Lys Xaa Trp Trp Glu Arg Trp Trp Arg Xaa Trp Pro Arg Lys Arg
1               5                   10                  15

Lys

<210> SEQ ID NO 10
<211> LENGTH: 17
<212> TYPE: PRT
<213> ORGANISM: Artificial Sequence
```

```
<220> FEATURE:
<223> OTHER INFORMATION: synthesized peptide VEPEP-3estap
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (5)..(5)
<223> OTHER INFORMATION: Xaa = non-natural amino acid used for the
      binding of a hydrocarbon staple
<220> FEATURE:
<221> NAME/KEY: MISC_FEATURE
<222> LOCATION: (12)..(12)
<223> OTHER INFORMATION: Xaa = non-natural amino acid used for the
      binding of a hydrocarbon staple

<400> SEQUENCE: 10

Xaa Arg Trp Trp Xaa Leu Trp Trp Arg Ser Trp Xaa Arg Leu Trp Arg
1               5                   10                  15

Arg

<210> SEQ ID NO 11
<211> LENGTH: 17
<212> TYPE: PRT
<213> ORGANISM: Artificial Sequence
<220> FEATURE:
<223> OTHER INFORMATION: synthesized peptide VEPEP-3
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (2)..(2)
<223> OTHER INFORMATION: Xaa = Lys, Arg or Leu
<220> FEATURE:
<221> NAME/KEY: MISC_FEATURE
<222> LOCATION: (3)..(3)
<223> OTHER INFORMATION: Xaa = Phe or Trp
<220> FEATURE:
<221> NAME/KEY: MISC_FEATURE
<222> LOCATION: (4)..(4)
<223> OTHER INFORMATION: Xaa = Phe, Trp or Tyr
<220> FEATURE:
<221> NAME/KEY: MISC_FEATURE
<222> LOCATION: (5)..(5)
<223> OTHER INFORMATION: Xaa = Glu, Arg or Ser
<220> FEATURE:
<221> NAME/KEY: MISC_FEATURE
<222> LOCATION: (6)..(6)
<223> OTHER INFORMATION: Xaa = Lys, Arg or Leu
<220> FEATURE:
<221> NAME/KEY: MISC_FEATURE
<222> LOCATION: (7)..(7)
<223> OTHER INFORMATION: Xaa = Phe or Trp
<220> FEATURE:
<221> NAME/KEY: MISC_FEATURE
<222> LOCATION: (8)..(8)
<223> OTHER INFORMATION: Xaa = Phe, Trp or Tyr
<220> FEATURE:
<221> NAME/KEY: MISC_FEATURE
<222> LOCATION: (9)..(9)
<223> OTHER INFORMATION: Xaa = Arg, Thr or Ser
<220> FEATURE:
<221> NAME/KEY: MISC_FEATURE
<222> LOCATION: (10)..(10)
<223> OTHER INFORMATION: Xaa = Glu, Arg or Ser
<220> FEATURE:
<221> NAME/KEY: MISC_FEATURE
<222> LOCATION: (11)..(11)
<223> OTHER INFORMATION: Xaa = Phe or Trp
<220> FEATURE:
<221> NAME/KEY: MISC_FEATURE
<222> LOCATION: (12)..(12)
<223> OTHER INFORMATION: Xaa = none, Phe or Trp
```

```
<220> FEATURE:
<221> NAME/KEY: MISC_FEATURE
<222> LOCATION: (13)..(13)
<223> OTHER INFORMATION: Xaa = Pro or Arg
<220> FEATURE:
<221> NAME/KEY: MISC_FEATURE
<222> LOCATION: (14)..(14)
<223> OTHER INFORMATION: Xaa = Arg or Leu
<220> FEATURE:
<221> NAME/KEY: MISC_FEATURE
<222> LOCATION: (15)..(15)
<223> OTHER INFORMATION: Xaa = Lys, Trp or Arg
<220> FEATURE:
<221> NAME/KEY: MISC_FEATURE
<222> LOCATION: (16)..(16)
<223> OTHER INFORMATION: Xaa = Arg or Phe
<220> FEATURE:
<221> NAME/KEY: MISC_FEATURE
<222> LOCATION: (17)..(17)
<223> OTHER INFORMATION: Xaa = Arg or Lys

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 12
<211> LENGTH: 16
<212> TYPE: PRT
<213> ORGANISM: Artificial Sequence
<220> FEATURE:
<223> OTHER INFORMATION: synthesized peptide VEPEP-3a-d
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (2)..(2)
<223> OTHER INFORMATION: Xaa = Arg or Lys
<220> FEATURE:
<221> NAME/KEY: MISC_FEATURE
<222> LOCATION: (4)..(4)
<223> OTHER INFORMATION: Xaa = Phe, Trp or Tyr
<220> FEATURE:
<221> NAME/KEY: MISC_FEATURE
<222> LOCATION: (6)..(6)
<223> OTHER INFORMATION: Xaa = Arg or Lys
<220> FEATURE:
<221> NAME/KEY: MISC_FEATURE
<222> LOCATION: (8)..(8)
<223> OTHER INFORMATION: Xaa = Phe, Trp or Tyr
<220> FEATURE:
<221> NAME/KEY: MISC_FEATURE
<222> LOCATION: (9)..(9)
<223> OTHER INFORMATION: Xaa = Thr or Arg
<220> FEATURE:
<221> NAME/KEY: MISC_FEATURE
<222> LOCATION: (10)..(10)
<223> OTHER INFORMATION: Xaa = Glu or Arg
<220> FEATURE:
<221> NAME/KEY: MISC_FEATURE
<222> LOCATION: (11)..(11)
<223> OTHER INFORMATION: Xaa = Trp or Phe
<220> FEATURE:
<221> NAME/KEY: MISC_FEATURE
<222> LOCATION: (14)..(14)
<223> OTHER INFORMATION: Xaa = Arg or Lys
<220> FEATURE:
<221> NAME/KEY: MISC_FEATURE
<222> LOCATION: (16)..(16)
<223> OTHER INFORMATION: Xaa = Arg or Lys
```

```
<400> SEQUENCE: 12

Xaa Xaa Trp Xaa Glu Xaa Trp Xaa Xaa Xaa Xaa Pro Arg Xaa Arg Xaa
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: synthesized peptide VEPEP-3e-h
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (2)..(2)
<223> OTHER INFORMATION: Xaa = Lys, Arg or Leu
<220> FEATURE:
<221> NAME/KEY: MISC_FEATURE
<222> LOCATION: (3)..(3)
<223> OTHER INFORMATION: Xaa = Phe or Trp
<220> FEATURE:
<221> NAME/KEY: MISC_FEATURE
<222> LOCATION: (5)..(5)
<223> OTHER INFORMATION: Xaa = Arg or Ser
<220> FEATURE:
<221> NAME/KEY: MISC_FEATURE
<222> LOCATION: (6)..(6)
<223> OTHER INFORMATION: Xaa = Leu or Arg
<220> FEATURE:
<221> NAME/KEY: MISC_FEATURE
<222> LOCATION: (7)..(7)
<223> OTHER INFORMATION: Xaa = Phe or Trp
<220> FEATURE:
<221> NAME/KEY: MISC_FEATURE
<222> LOCATION: (9)..(9)
<223> OTHER INFORMATION: Xaa = Arg or Ser
<220> FEATURE:
<221> NAME/KEY: MISC_FEATURE
<222> LOCATION: (10)..(10)
<223> OTHER INFORMATION: Xaa = Arg or Ser
<220> FEATURE:
<221> NAME/KEY: MISC_FEATURE
<222> LOCATION: (12)..(12)
<223> OTHER INFORMATION: Xaa = Phe or Trp
<220> FEATURE:
<221> NAME/KEY: MISC_FEATURE
<222> LOCATION: (13)..(13)
<223> OTHER INFORMATION: Xaa = Arg or Pro
<220> FEATURE:
<221> NAME/KEY: MISC_FEATURE
<222> LOCATION: (14)..(14)
<223> OTHER INFORMATION: Xaa = Leu or Arg
<220> FEATURE:
<221> NAME/KEY: MISC_FEATURE
<222> LOCATION: (16)..(16)
<223> OTHER INFORMATION: Xaa = Arg or Phe

<400> SEQUENCE: 13

Xaa Xaa Xaa Trp Xaa Xaa Xaa Trp Xaa Xaa Trp Xaa Xaa Xaa Trp Xaa
1               5                   10                  15
Arg

<210> SEQ ID NO 14
<211> LENGTH: 16
<212> TYPE: PRT
<213> ORGANISM: Artificial Sequence
<220> FEATURE:
<223> OTHER INFORMATION: synthesized peptide VEPEP-3-Funct-1
```

```
<220> FEATURE:
<221> NAME/KEY: MISC_FEATURE
<222> LOCATION: (1)..(1)
<223> OTHER INFORMATION: residue covalently linked to Cholesterol,
      Pegylation, stearyl, palmitoyl, small FC or FAB fragments,
      nanobody, nitrilotriacetic acid (2 x NTA), or tissues targeting
      peptides
<220> FEATURE:
<221> NAME/KEY: MISC_FEATURE
<222> LOCATION: (16)..(16)
<223> OTHER INFORMATION: residue covalently linked to CH2-CH2-SH

<400> SEQUENCE: 14

Leu Trp Trp Arg Arg Trp Trp Ser Arg Trp Trp Pro Arg Trp Arg Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthesized peptide VEPEP-3-Funct-2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (16)..(16)
<223> OTHER INFORMATION: residue covalently linked to CH2-CH2-S-S-Z,
      with Z = Cholesterol, Pegylation, stearyl, palmitoyl, small FC or
      FAB fragments, nanobody, nitrilotriacetic acid (2 x NTA), or
      tissues targeting peptides

<400> SEQUENCE: 15

Leu Trp Trp Arg Arg Trp Trp Ser Arg Trp Trp Pro Arg Trp Arg Arg
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: synthesized peptide VEPEP-3-Funct-3
<220> FEATURE:
<221> NAME/KEY: MISC_FEATURE
<222> LOCATION: (1)..(1)
<223> OTHER INFORMATION: residue covalently linked to Cholesterol,
      Pegylation, stearyl, palmitoyl, small FC or FAB fragments,
      nanobody, nitrilotriacetic acid (2 x NTA), or tissues targeting
      peptides
<220> FEATURE:
<221> NAME/KEY: MISC_FEATURE
<222> LOCATION: (2)..(2)
<223> OTHER INFORMATION: Xaa = Trp or Phe
<220> FEATURE:
<221> NAME/KEY: MISC_FEATURE
<222> LOCATION: (6)..(6)
<223> OTHER INFORMATION: Xaa = Trp or Phe
<220> FEATURE:
<221> NAME/KEY: MISC_FEATURE
<222> LOCATION: (9)..(9)
<223> OTHER INFORMATION: residue covalently linked to CH2-CH2-SH

<400> SEQUENCE: 16

Trp Xaa Arg Leu Trp Xaa Arg Leu Arg
1               5

<210> SEQ ID NO 17
<211> LENGTH: 9
<212> TYPE: PRT
<213> ORGANISM: Artificial Sequence
```

-continued

```
<220> FEATURE:
<223> OTHER INFORMATION: synthesized peptide VEPEP-3-Funct-4
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (2)..(2)
<223> OTHER INFORMATION: Xaa = Trp or Phe
<220> FEATURE:
<221> NAME/KEY: MISC_FEATURE
<222> LOCATION: (6)..(6)
<223> OTHER INFORMATION: Xaa = Trp or Phe
<220> FEATURE:
<221> NAME/KEY: MISC_FEATURE
<222> LOCATION: (9)..(9)
<223> OTHER INFORMATION: residue covalently linked to CH2-CH2-S-S-Z,
      with Z = Cholesterol, Pegylation, stearyl, palmitoyl, small FC or
      FAB fragments, nanobody, nitrilotriacetic acid (2 x NTA), or
      tissues targeting peptides

<400> SEQUENCE: 17

Trp Xaa Arg Leu Trp Xaa Arg Leu Arg
1               5

<210> SEQ ID NO 18
<211> LENGTH: 18
<212> TYPE: DNA
<213> ORGANISM: Artificial Sequence
<220> FEATURE:
<223> OTHER INFORMATION: synthesized oligonucleotide Cyc-B1a

<400> SEQUENCE: 18
tgccatcggg cttggagg                                                 18

<210> SEQ ID NO 19
<211> LENGTH: 18
<212> TYPE: DNA
<213> ORGANISM: Artificial Sequence
<220> FEATURE:
<223> OTHER INFORMATION: synthesized oligonucleotide Cyc-Bct

<400> SEQUENCE: 19
tgccatcaag cttagagg                                                 18

<210> SEQ ID NO 20
<211> LENGTH: 12
<212> TYPE: PRT
<213> ORGANISM: Artificial Sequence
<220> FEATURE:
<223> OTHER INFORMATION: synthesized peptide C2

<400> SEQUENCE: 20

Lys Lys Gln Val Leu Ala Met Glu His Leu Val Thr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: synthesized peptide C2S

<400> SEQUENCE: 21

Val Thr Leu Met Glu Ala Lys Lys Gln Val Leu Thr
1               5                   10
```

```
<210> SEQ ID NO 22
<211> LENGTH: 12
<212> TYPE: PRT
<213> ORGANISM: Artificial Sequence
<220> FEATURE:
<223> OTHER INFORMATION: synthesized peptide C4

<400> SEQUENCE: 22

Lys Lys Gln Val Arg Met Ala His Leu Val Leu Thr
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthesized peptide C4C

<400> SEQUENCE: 23

Cys Lys Lys Gln Val Arg Met Ala His Leu Val Leu Thr Cys
1               5                   10

<210> SEQ ID NO 24
<211> LENGTH: 8
<212> TYPE: PRT
<213> ORGANISM: Artificial Sequence
<220> FEATURE:
<223> OTHER INFORMATION: synthesized peptide PC4

<400> SEQUENCE: 24

Arg Trp Thr Glu Trp Glu Trp Trp
1               5

<210> SEQ ID NO 25
<211> LENGTH: 8
<212> TYPE: PRT
<213> ORGANISM: Artificial Sequence
<220> FEATURE:
<223> OTHER INFORMATION: synthesized peptide PC4S

<400> SEQUENCE: 25

Thr Trp Phe Thr Glu Trp Phe Thr
1               5

<210> SEQ ID NO 26
<211> LENGTH: 8
<212> TYPE: PRT
<213> ORGANISM: Artificial Sequence
<220> FEATURE:
<223> OTHER INFORMATION: synthesized peptide PC6

<400> SEQUENCE: 26

Lys Trp Glu Thr Trp Trp Glu Thr
1               5

<210> SEQ ID NO 27
<211> LENGTH: 8
<212> TYPE: PRT
<213> ORGANISM: Artificial Sequence
<220> FEATURE:
<223> OTHER INFORMATION: synthesized peptide PC6S

<400> SEQUENCE: 27

Lys Ala Glu Thr Trp Ala Glu Thr
1               5
```

```
<210> SEQ ID NO 28
<211> LENGTH: 20
<212> TYPE: PRT
<213> ORGANISM: Artificial Sequence
<220> FEATURE:
<223> OTHER INFORMATION: synthesized peptide CADY-1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (20)..(20)
<223> OTHER INFORMATION: residue covalently linked to cysteamide

<400> SEQUENCE: 28

Gly Leu Trp Arg Ala Leu Trp Arg Leu Leu Arg Ser Leu Trp Arg Leu
1               5                   10                  15

Leu Trp Lys Ala
            20

<210> SEQ ID NO 29
<211> LENGTH: 19
<212> TYPE: PRT
<213> ORGANISM: Artificial Sequence
<220> FEATURE:
<223> OTHER INFORMATION: synthesized peptide VEPEP-6a
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (19)..(19)
<223> OTHER INFORMATION: residue covalently linked to cysteamide

<400> SEQUENCE: 29

Xaa Leu Phe Arg Ala Leu Trp Arg Leu Leu Arg Ser Leu Trp Arg Leu
1               5                   10                  15

Leu Trp Lys

<210> SEQ ID NO 30
<211> LENGTH: 20
<212> TYPE: PRT
<213> ORGANISM: Artificial Sequence
<220> FEATURE:
<223> OTHER INFORMATION: synthesized peptide VEPEP-6b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (20)..(20)
<223> OTHER INFORMATION: residue covalently linked to cysteamide

<400> SEQUENCE: 30

Xaa Leu Trp Arg Ala Leu Trp Arg Leu Trp Arg Ser Leu Trp Arg Leu
1               5                   10                  15

Leu Trp Lys Ala
            20
```

```
<210> SEQ ID NO 31
<211> LENGTH: 20
<212> TYPE: PRT
<213> ORGANISM: Artificial Sequence
<220> FEATURE:
<223> OTHER INFORMATION: synthesized peptide VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (20)..(20)
<223> OTHER INFORMATION: residue covalently linked to cysteamide

<400> SEQUENCE: 31

Xaa Leu Trp Arg Ala Leu Trp Arg Leu Leu Arg Ser Leu Trp Arg Leu
1               5                   10                  15

Trp Arg Lys Ala
            20

<210> SEQ ID NO 32
<211> LENGTH: 20
<212> TYPE: PRT
<213> ORGANISM: Artificial Sequence
<220> FEATURE:
<223> OTHER INFORMATION: synthesized peptide VEPEP-6d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (20)..(20)
<223> OTHER INFORMATION: residue covalently linked to cysteamide

<400> SEQUENCE: 32

Xaa Leu Trp Arg Ala Leu Trp Arg Leu Trp Arg Ser Leu Trp Arg Leu
1               5                   10                  15

Trp Arg Lys Ala
            20

<210> SEQ ID NO 33
<211> LENGTH: 20
<212> TYPE: PRT
<213> ORGANISM: Artificial Sequence
<220> FEATURE:
<223> OTHER INFORMATION: synthesized peptide VEPEP-6e
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (20)..(20)
<223> OTHER INFORMATION: residue covalently linked to cysteamide
```

```
<400> SEQUENCE: 33

Xaa Leu Trp Arg Ala Leu Trp Arg Leu Leu Arg Ala Leu Trp Arg Leu
1               5                   10                  15

Leu Trp Lys Ala
            20

<210> SEQ ID NO 34
<211> LENGTH: 20
<212> TYPE: PRT
<213> ORGANISM: Artificial Sequence
<220> FEATURE:
<223> OTHER INFORMATION: synthesized peptide VEPEP-6f
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (20)..(20)
<223> OTHER INFORMATION: residue covalently linked to cysteamide

<400> SEQUENCE: 34

Xaa Leu Trp Arg Ala Leu Trp Arg Leu Leu Arg Asn Leu Trp Arg Leu
1               5                   10                  15

Leu Trp Lys Ala
            20

<210> SEQ ID NO 35
<211> LENGTH: 20
<212> TYPE: PRT
<213> ORGANISM: Artificial Sequence
<220> FEATURE:
<223> OTHER INFORMATION: synthesized peptide VEPEP-9a1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (20)..(20)
<223> OTHER INFORMATION: residue covalently linked to cysteamide

<400> SEQUENCE: 35

Xaa Leu Arg Trp Trp Leu Arg Trp Ala Ser Arg Trp Phe Ser Arg Trp
1               5                   10                  15

Ala Trp Trp Arg
            20

<210> SEQ ID NO 36
<211> LENGTH: 20
<212> TYPE: PRT
<213> ORGANISM: Artificial Sequence
<220> FEATURE:
<223> OTHER INFORMATION: synthesized peptide VEPEP-9a2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
```

```
<220> FEATURE:
<221> NAME/KEY: MISC_FEATURE
<222> LOCATION: (20)..(20)
<223> OTHER INFORMATION: residue covalently linked to cysteamide

<400> SEQUENCE: 36

Xaa Leu Arg Trp Trp Leu Arg Trp Ala Ser Arg Trp Ala Ser Arg Trp
1               5                   10                  15

Ala Trp Phe Arg
            20

<210> SEQ ID NO 37
<211> LENGTH: 19
<212> TYPE: PRT
<213> ORGANISM: Artificial Sequence
<220> FEATURE:
<223> OTHER INFORMATION: synthesized peptide VEPEP-9b1
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (19)..(19)
<223> OTHER INFORMATION: residue covalently linked to cysteamide

<400> SEQUENCE: 37

Xaa Arg Trp Trp Leu Arg Trp Ala Ser Arg Trp Ala Leu Ser Trp Arg
1               5                   10                  15

Trp Trp Arg

<210> SEQ ID NO 38
<211> LENGTH: 19
<212> TYPE: PRT
<213> ORGANISM: Artificial Sequence
<220> FEATURE:
<223> OTHER INFORMATION: synthesized peptide VEPEP-9b2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (19)..(19)
<223> OTHER INFORMATION: residue covalently linked to cysteamide

<400> SEQUENCE: 38

Xaa Arg Trp Trp Leu Arg Trp Ala Ser Arg Trp Phe Leu Ser Trp Arg
1               5                   10                  15

Trp Trp Arg

<210> SEQ ID NO 39
<211> LENGTH: 19
<212> TYPE: PRT
<213> ORGANISM: Artificial Sequence
<220> FEATURE:
<223> OTHER INFORMATION: synthesized peptide VEPEP-9c1
<220> FEATURE:
<221> NAME/KEY: MISC_FEATURE
<222> LOCATION: (1)..(1)
<223> OTHER INFORMATION: acetylated residue
```

```
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (19)..(19)
<223> OTHER INFORMATION: residue covalently linked to cysteamide

<400> SEQUENCE: 39

Xaa Arg Trp Trp Leu Arg Trp Ala Pro Arg Trp Phe Pro Ser Trp Arg
1               5                   10                  15

Trp Trp Arg

<210> SEQ ID NO 40
<211> LENGTH: 19
<212> TYPE: PRT
<213> ORGANISM: Artificial Sequence
<220> FEATURE:
<223> OTHER INFORMATION: synthesized peptide VEPEP-9c2
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (19)..(19)
<223> OTHER INFORMATION: residue covalently linked to cysteamide

<400> SEQUENCE: 40

Xaa Arg Trp Trp Leu Arg Trp Ala Ser Arg Trp Ala Pro Ser Trp Arg
1               5                   10                  15

Trp Trp Arg

<210> SEQ ID NO 41
<211> LENGTH: 15
<212> TYPE: PRT
<213> ORGANISM: Artificial Sequence
<220> FEATURE:
<223> OTHER INFORMATION: synthesized peptide VEPEP-9d
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (15)..(15)
<223> OTHER INFORMATION: residue covalently linked to cysteamide

<400> SEQUENCE: 41

Xaa Trp Trp Arg Trp Trp Ala Ser Trp Ala Arg Ser Trp Trp Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: synthesized peptide VEPEP-9e
<220> FEATURE:
<221> NAME/KEY: MISC_FEATURE
<222> LOCATION: (1)..(1)
<223> OTHER INFORMATION: acetylated residue
```

```
<220> FEATURE:
<221> NAME/KEY: MISC_FEATURE
<222> LOCATION: (1)..(1)
<223> OTHER INFORMATION: Xaa

-continued

```
<210> SEQ ID NO 45
<211> LENGTH: 19
<212> TYPE: PRT
<213> ORGANISM: Artificial Sequence
<220> FEATURE:
<223> OTHER INFORMATION: synthesized peptide ST-VEPEP-6aa
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (8)..(8)
<223> OTHER INFORMATION: Xaa =  Arg, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Arg residue
      at position 8 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 45

Xaa Leu Phe Leu Ala Arg Trp Xaa Leu Leu Arg Xaa Leu Trp Arg Leu
1               5                   10                  15

Leu Trp Lys

<210> SEQ ID NO 46
<211> LENGTH: 19
<212> TYPE: PRT
<213> ORGANISM: Artificial Sequence
<220> FEATURE:
<223> OTHER INFORMATION: synthesized peptide ST-VEPEP-6ab
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (8)..(8)
<223> OTHER INFORMATION: Xaa =  Ser, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Ser residue
      at position 8 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 46

Xaa Leu Phe Arg Ala Leu Trp Xaa Leu Leu Arg Xaa Leu Trp Arg Leu
1               5                   10                  15

Leu Trp Lys

<210> SEQ ID NO 47
<211> LENGTH: 19
<212> TYPE: PRT
<213> ORGANISM: Artificial Sequence
```

```
<220> FEATURE:
<223> OTHER INFORMATION: synthesized peptide ST-VEPEP-6ad
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (8)..(8)
<223> OTHER INFORMATION: Xaa =  Ser, which is linked to the Ser residue
      at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Ser residue
      at position 8
    by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 47

Xaa Leu Phe Leu Ala Arg Trp Xaa Leu Leu Arg Xaa Leu Trp Arg Leu
1               5                   10                  15

Leu Trp Lys

<210> SEQ ID NO 48
<211> LENGTH: 19
<212> TYPE: PRT
<213> ORGANISM: Artificial Sequence
<220> FEATURE:
<223> OTHER INFORMATION: synthesized peptide ST-VEPEP-6b
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (11)..(11)
<223> OTHER INFORMATION: Xaa =  Arg, which is linked to the Ser residue
      at position 15 by a hydrocarbon linkage
<220> FEATURE:
<221> NAME/KEY: MISC_FEATURE
<222> LOCATION: (15)..(15)
<223> OTHER INFORMATION: Xaa =  Ser, which is linked to the Arg residue
      at position 11 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 48

Xaa Leu Phe Arg Ala Leu Trp Arg Leu Leu Xaa Ser Leu Trp Xaa Leu
1               5                   10                  15

Leu Trp Lys

<210> SEQ ID NO 49
<211> LENGTH: 19
<212> TYPE: PRT
<213> ORGANISM: Artificial Sequence
<220> FEATURE:
<223> OTHER INFORMATION: synthesized peptide ST-VEPEP-6ba
```

```
<220> FEATURE:
<221> NAME/KEY: MISC_FEATURE
<222> LOCATION: (1)..(1)
<223> OTHER INFORMATION: acetylated residue
<220> FEATURE:
<221> N

```
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (11)..(11)
<223> OTHER INFORMATION: Xaa =  Ser, which is linked to the Ser residue
      at position 15 by a hydrocarbon linkage
<220> FEATURE:
<221> NAME/KEY: MISC_FEATURE
<222> LOCATION: (15)..(15)
<223> OTHER INFORMATION: Xaa =  Ser, which is linked to the Ser residue
      at position 11 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 51

Xaa Leu Phe Leu Ala Arg Trp Arg Leu Leu Xaa Ser Leu Trp Xaa Leu
1               5                   10                  15

Leu Trp Lys

<210> SEQ ID NO 52
<211> LENGTH: 19
<212> TYPE: PRT
<213> ORGANISM: Artificial Sequence
<220> FEATURE:
<223> OTHER INFORMATION: synthesized peptide ST-VEPEP-6c
<220> FEATURE:
<221> NAME/KEY: MISC_FEATURE
<222> LOCATION: (1)..(1)
<223> OTHER INFORMATION: acetylated residue
<220> FEATURE:
<221> NAME/KEY: MISC_FEATURE
<222> LOCATION: (1)..(1)
<223> OTHER INFORMATION: Xaa = beta-Alanine or Serine
<220> FEATURE:
<221> NAME/KEY: MISC_FEATURE
<222> LOCATION: (5)..(5)
<223> OTHER INFORMATION: Xaa =  Arg, which is linked to the Ser residue
    at position 12 by a hydrocarbon linkage
<220> FEATURE:
<221> NAME/KEY: MISC_FEATURE
<222> LOCATION: (12)..(12)
<223> OTHER INFORMATION: Xaa =  Ser, which is linked to the Arg residue
      at position 5 by a hydrocarbon linkage
<220> FEATURE:
<221> NAME/KEY: MISC_FEATURE
<222> LOCATION: (19)..(19)
<223> OTHER INFORMATION: residue covalently linked to cysteamide

<400> SEQUENCE: 52

Xaa Leu Phe Ala Xaa Leu Trp Arg Leu Leu Arg Xaa Leu Trp Arg Leu
1               5                   10                  15

Leu Trp Lys
```

CELL PENETRATING PEPTIDES FOR INTRACELLULAR DELIVERY OF MOLECULES

CROSS REFERENCE TO RELATED APPLICATIONS

This application is a Continuation of U.S. patent application Ser. No. 14/433,570, filed on Apr. 3, 2015, which is the National Stage filing of PCT/EP2013/070676, entitled "CELL PENETRATING PEPTIDES FOR INTRACELLULAR DELIVERY OF MOLECULES" with the International Filing Date of Oct. 4, 2013, each of which is hereby incorporated by reference in its entirety for all purposes as if put forth in full below. The International Application PCT/EP2013/070676 claims the benefit of priority from PCT/IB2012/055343, filed on Oct. 4, 2012.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737372000501SeqList.txt, date recorded: Feb. 9, 2017 size: 29 KB).

FIELD OF THE INVENTION

The present invention pertains to the field of intracellular delivery of molecules such as nucleic acids and small hydrophobic molecules. In particular, the invention relates to a new cell-penetrating peptide (CPP) family, which exhibits high efficacy, low toxicity and a natural tropism for brain and lymphe node tissues.

BACKGROUND OF THE INVENTION

Although small molecules remain the major drugs used in clinic, in numerous cases, their therapeutic impact has reached limitations such as insufficient capability to reach targets, lack of specificity, requirement for high doses leading to toxicity and major side effects. Over the past ten years, in order to circumvent limitations of small molecules and of gene-based therapies, we have witnessed a dramatic acceleration in the discovery of larger therapeutic molecules such as proteins, peptides and nucleic acids which present a high specificity for their target but do not follow Lipinski's rules. Pharmaceutical potency of these molecules remains restricted by their poor stability in vivo and by their low uptake in cells. Therefore, "delivery" has become a central piece of the therapeutic puzzle and new milestones have been established to validate delivery strategies: (a) lack of toxicity, (b) efficiency at low doses in vivo, (c) easy to handle for therapeutic applications (d) rapid endosomal release and (e) ability to reach the target. Although viral delivery strategies had given much hope for gene and cellular therapies, their clinical application has suffered from side- and toxicity-effects [1,2]. Researches were mainly focused on the development of non-viral strategies, and different methods have been proposed including lipid, polycationic nanoparticles and peptide-based formulations, but only few of these technologies have been efficient in vivo and have reached the clinic. Cell Penetrating Peptides (CPP) are one of the most promising non-viral strategies. Although definition of CPPs is constantly evolving, they are generally described as short peptides of less than 30 amino acids either derived from proteins or from chimeric sequences. They are usually amphipathic and possess a net positive charge [3-5]. CPPs are able to penetrate biological membranes, to trigger the movement of various biomolecules across cell membranes into the cytoplasm and to improve their intracellular routing, thereby facilitating interactions with the target. CPPs can be subdivided into two main classes, the first requiring chemical linkage with the cargo and the second involving the formation of stable, non-covalent complexes. CPPs from both strategies have been reported to favour the delivery of a large panel of cargos (plasmid DNA, oligonucleotide, siRNA, PNA, protein, peptide, liposome, nanoparticle . . . ) into a wide variety of cell types and in vivo models [3-7].

Twenty years ago, the concept of protein transduction domain (PTD) was proposed based on the observation that some proteins, mainly transcription factors, could shuttle within cells and from one cell to another [for review see ref 3,4]. The first observation was made in 1988, by Frankel and Pabo. They showed that the transcription-transactivating (Tat) protein of HIV-1 could enter cells and translocate into the nucleus. In 1991, the group of Prochiantz reached the same conclusions with the *Drosophila* Antennapedia homeodomain and demonstrated that this domain was internalized by neuronal cells. These works were at the origin of the discovery in 1994 of the first Protein Transduction Domain: a 16 mer-peptide derived from the third helix of the homeodomain of Antennapedia named Penetratin. In 1997, the group of Lebleu identified the minimal sequence of Tat required for cellular uptake and the first proofs-of-concept of the application of PTD in vivo, were reported by the group of Dowdy, for the delivery of small peptides and large proteins. Historically, the notion of Cell Penetrating Peptide (CPP) was introduced by the group of Langel, in 1998, with the design of the first chimeric peptide carrier, the Transportan, which derived from the N-terminal fragment of the neuropeptide galanin, linked to mastoparan, a wasp venom peptide. Transportan has been originally reported to improve the delivery of PNAs both in cultured cells and in vivo. In 1997, the group of Heitz and Divita proposed a new strategy involving CPP in the formation of stable but non-covalent complexes with their cargo [7]. The strategy was first based on the short peptide carrier (MPG) consisting of two domains: a hydrophilic (polar) domain and a hydrophobic (apolar) domain. MPG was designed for the delivery of nucleic acids [7]. The primary amphipathic peptide Pep-1 was then proposed for non-covalent delivery of proteins and peptides [8]. Then the groups of Wender and of Futaki demonstrated that polyarginine sequences (Arg8) are sufficient to drive small and large molecules into cells and in vivo. Ever since, many CPPs derived from natural or unnatural sequences have been identified and the list is constantly increasing. Peptides have been derived from VP22 protein of Herpes Simplex Virus, from calcitonin, from antimicrobial or toxin peptides, from proteins involved in cell cycle regulation, as well as from polyproline-rich peptides [reviews 4-6].

BRIEF DESCRIPTION OF THE DRAWINGS

FIGS. 1A, 1B, and 1C show the binding of VEPEP-3a (1A), VEPEP-3c (1B), and VEPEP-3g (1C) peptides with various fluorescently labeled cargoes (as determined by fluorescence spectroscopy).

Figure 3:
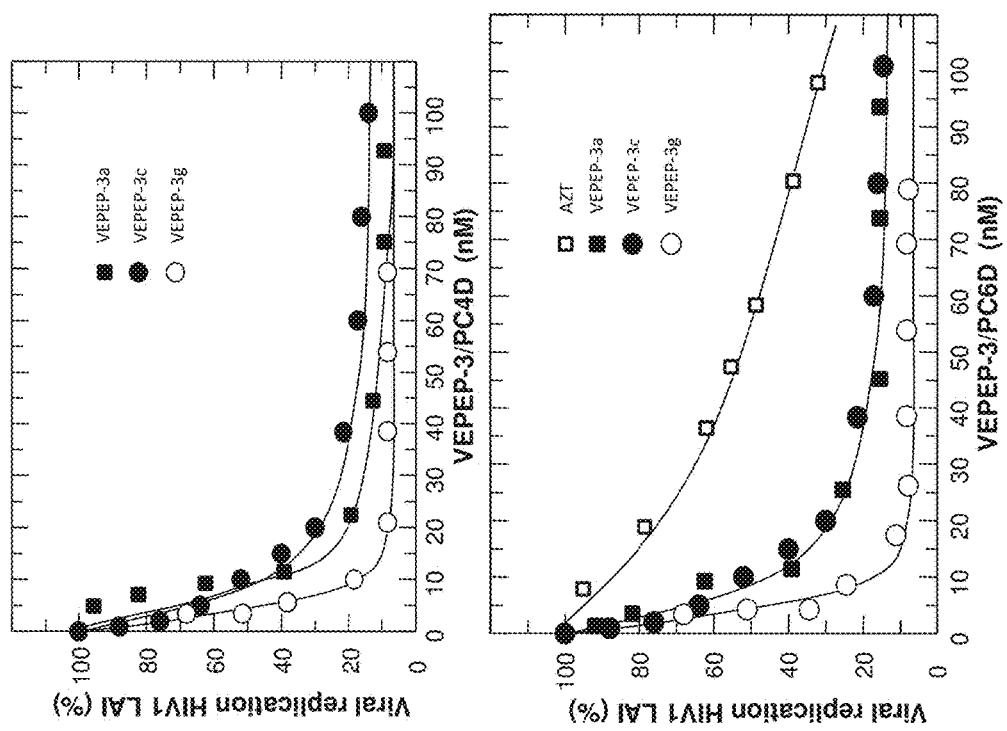

FIG. 3 shows the dose-response of VEPEP-3-mediated delivery of PC4D peptides on viral replication in HIV-infected PBMCs. VEPEP-3a, VEPEP-3c, and VEPEP-3g peptides were used for PC4D delivery.

Figure 4:
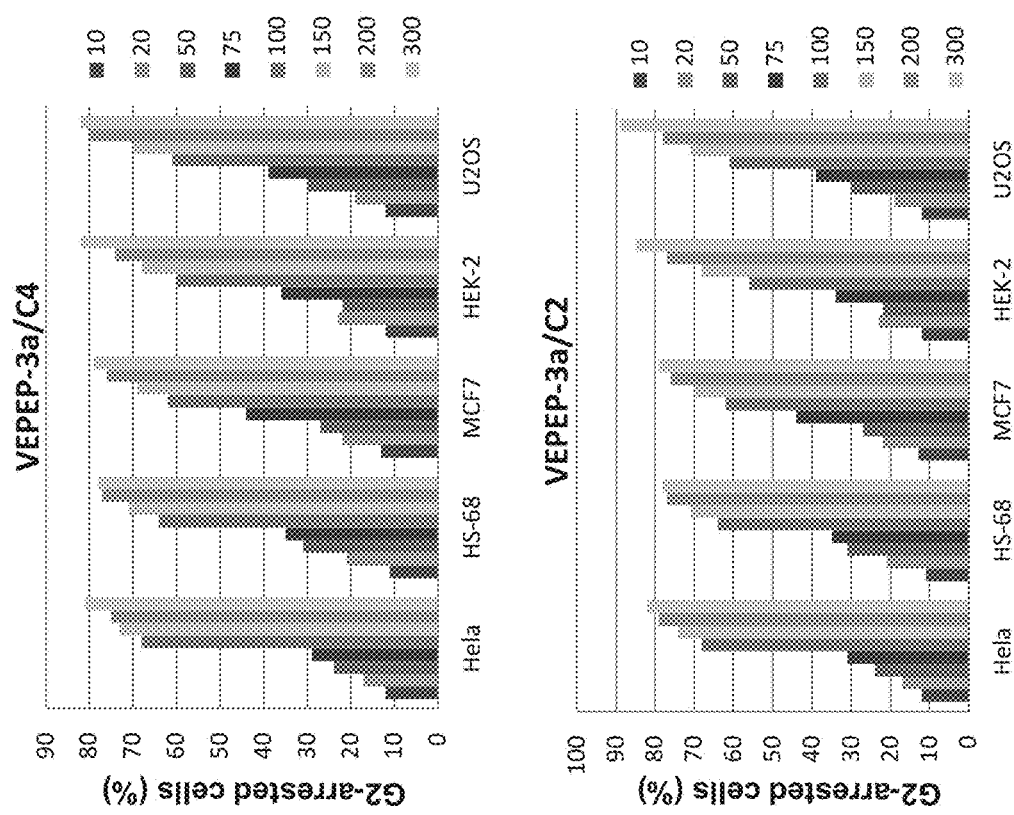

FIG. 4 shows the dose-response of VEPEP-3a-mediated delivery of C2 and C4 peptides on G2-arrest in Hela, MCF7, HEK-2, HS-68, and U2OS cells.

Figure 5:
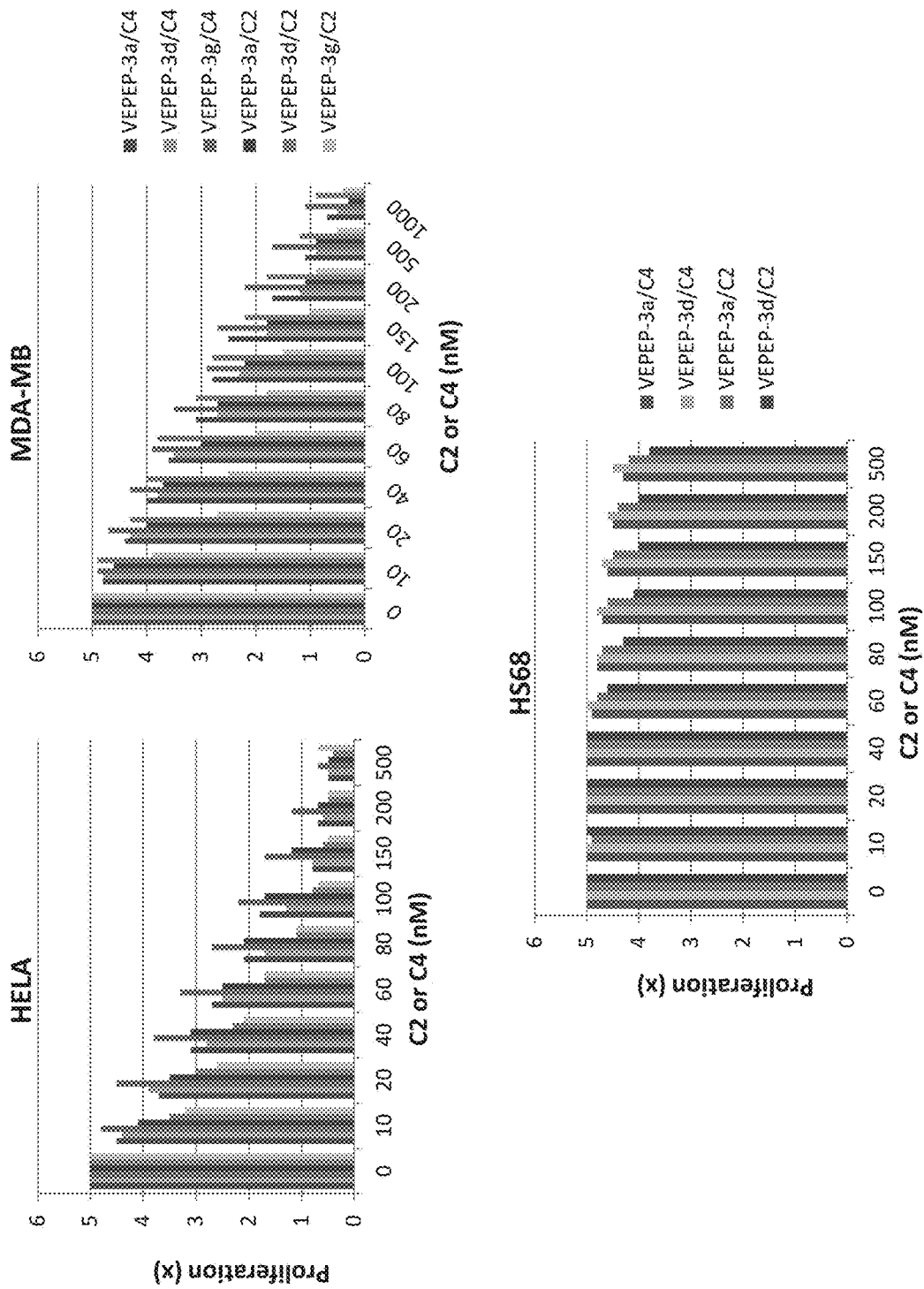

FIG. 5 shows the dose-response of VEPEP-3-mediated delivery of C2 and C4 peptides on proliferation in Hela, MDA-MB, and HS-68. VEPEP-3a, VEPEP-3d, and VEPEP-3g peptides were used for C2 and C4 delivery.

Figure 6:
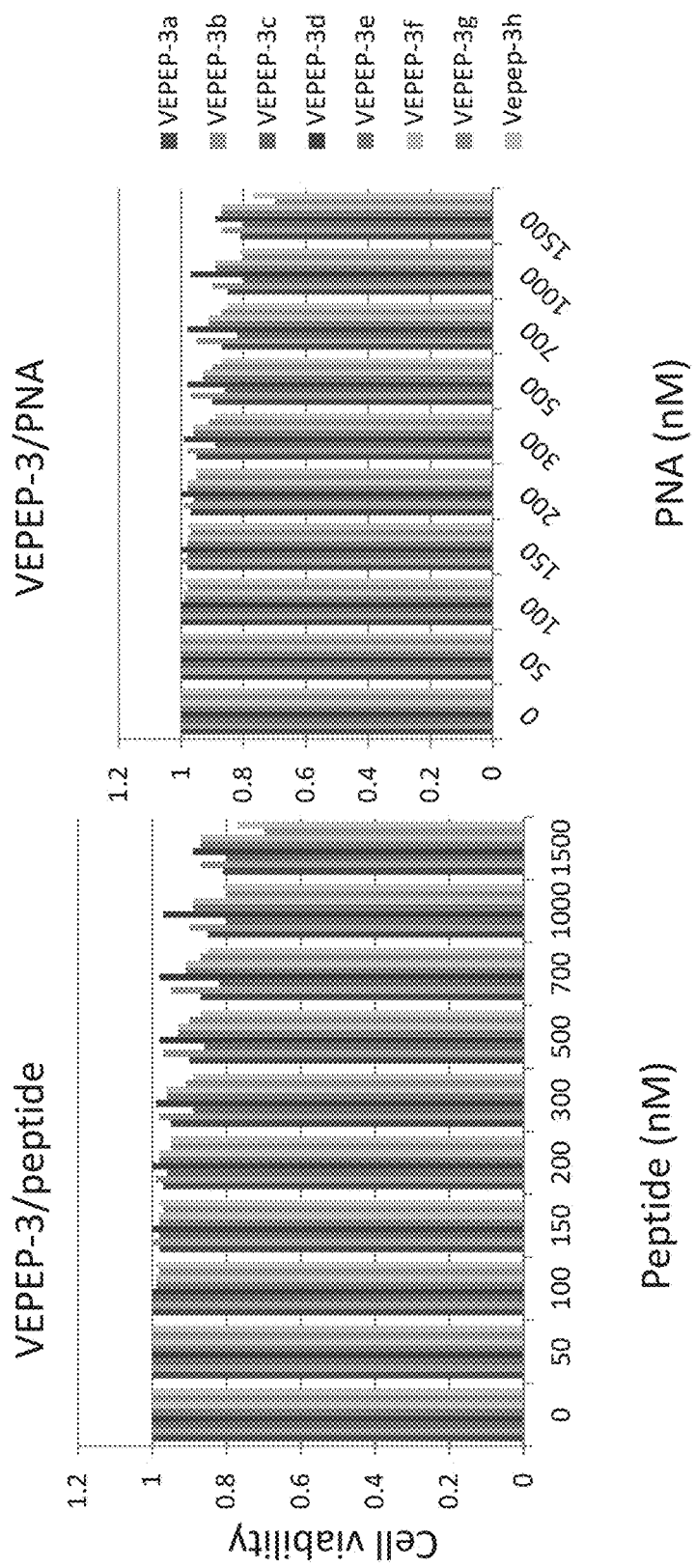

FIG. 6 shows the toxicity profile of VEPEP-3 particles on Hela and U2OS cells (as determined by MTT assay and by cyclophilin mRNA level). VEPEP-3a, VEPEP-3b, VEPEP-3c, VEPEP-3d, VEPEP-3e, VEPEP-3f, VEPEP-3g, and VEPEP-3h peptides were complexed with either short peptide or peptide nucleic acid (PNA) at 1:20 molar ratio.

Figure 7:
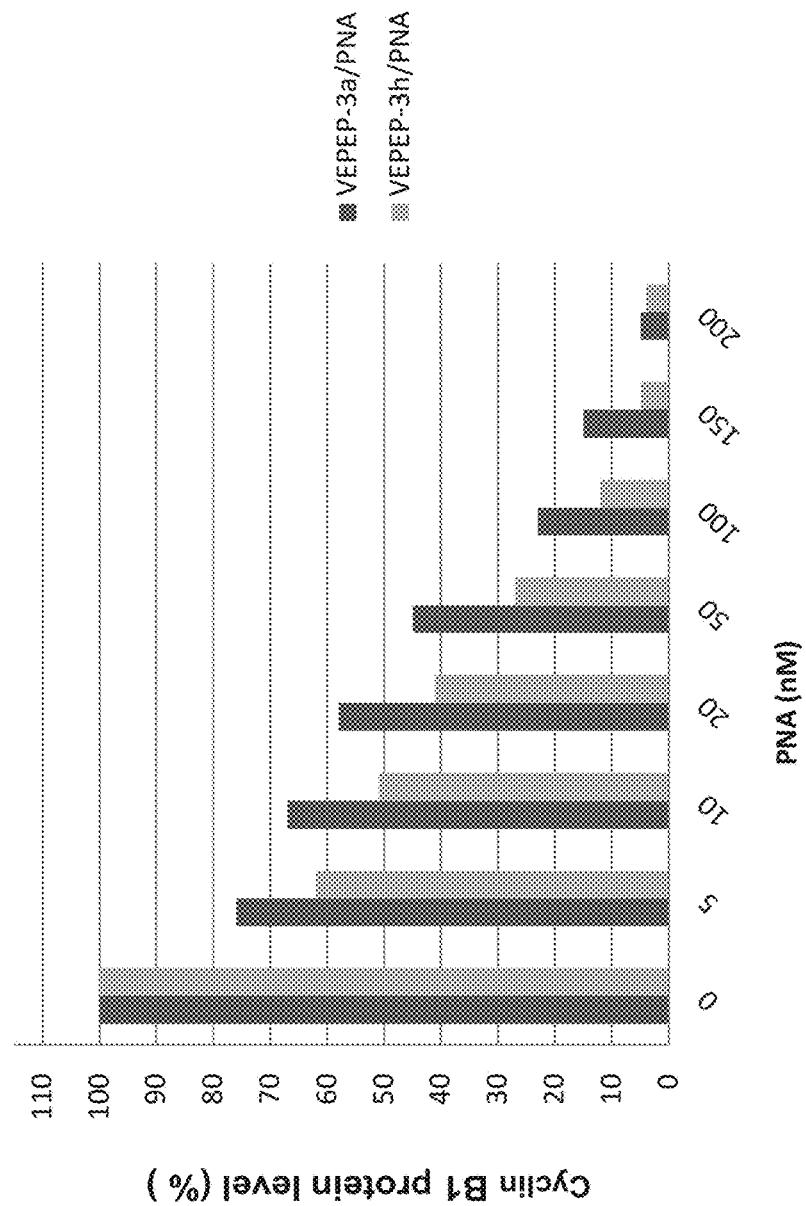

FIG. 7 shows the dose-response of VEPEP-3-mediated delivery of a Cyclin B1 antisense PNA on Cyclin B1 protein levels in cells. VEPEP-3a and VEPEP-3h peptides were used for PNA delivery.

FIG. 8 shows the dose-response of VEPEP-3-mediated delivery of doxorubicin, porphyrin, or taxol on cancer cell proliferation. VEPEP-3a, VEPEP-3c, and VEPEP-3g peptides were used for delivery in MCF-7 cells.

FIGS. 9A and 9B show schematics for the formation of NANOPEP particles having multilayer organization.

Figure 10A:
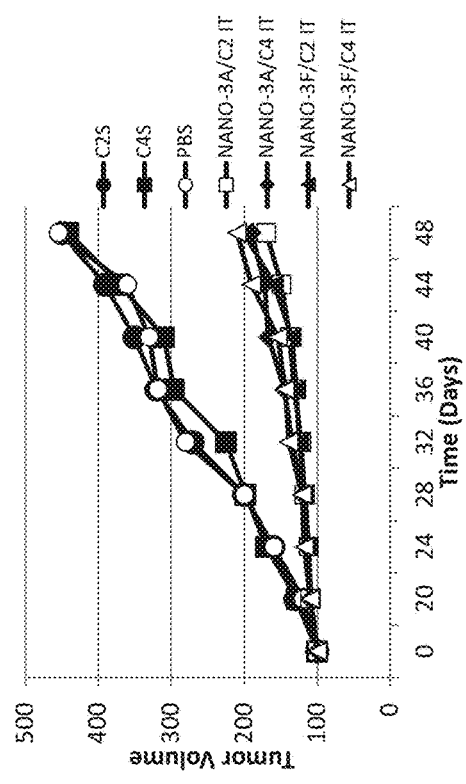
Figure 10B:
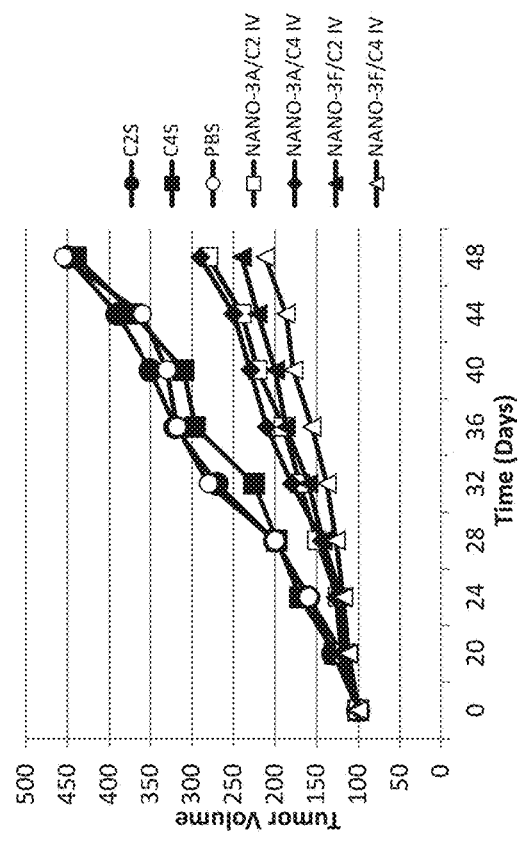

FIGS. 10A and 10B show reduction of tumor growth by administration of NANOPEP particles containing C2 or C4 peptide in PC3 xenograft mice. FIG. 10A shows results for intratumoral administration. FIG. 10B shows results for intravenous administration. NANO-3A/C2: VEPEP-3a/C2 core, coated with VEPEP-3a; NANO-3A/C4: VEPEP-3a/C4 core, coated with VEPEP-3a; NANO-3F/C2: VEPEP-3f/C2 core, coated with VEPEP-3f; NANO-3F/C4: VEPEP-3f/C4 core, coated with VEPEP-3f; C2S: VEPEP-3 NANOPEP particles with scrambled C2 peptide; C4S: VEPEP-3 NANOPEP particles with scrambled C4 peptide.

Figure 11:
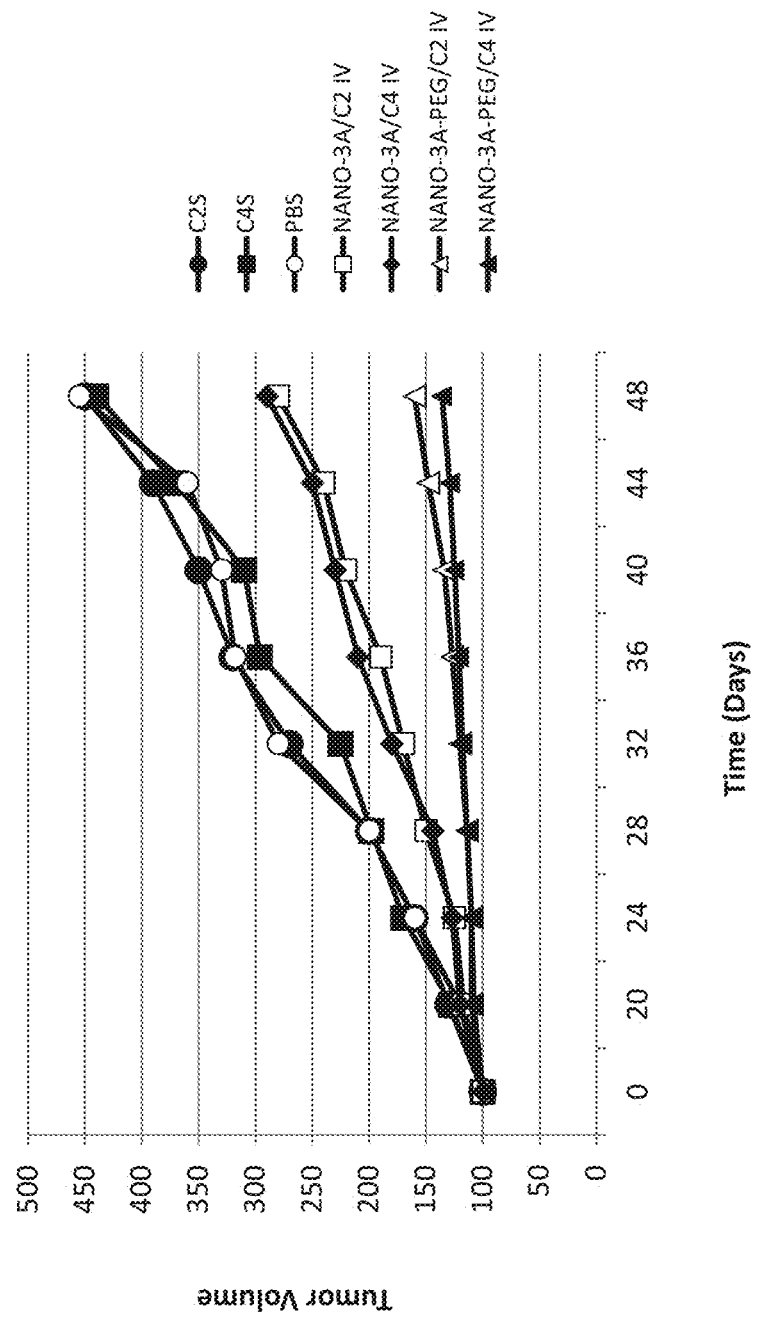

FIG. 11 shows reduction of tumor growth by intravenous administration of NANOPEP particles containing C2 or C4 peptide in SKB3-HEK2 xenograft mice. NANO-3A/C2: VEPEP-3a/C2 core, coated with VEPEP-3a; NANO-3A/C4: VEPEP-3a/C4 core, coated with VEPEP-3a; NANO-3A-PEG/C2: VEPEP-3a/C2 core, coated with PEG-VEPEP-3a; NANO-3A-PEG/C4: VEPEP-3a/C4 core, coated with PEG-VEPEP-3a; C2S: VEPEP-3 NANOPEP particles with scrambled C2 peptide; C4S: VEPEP-3 NANOPEP particles with scrambled C4 peptide.

Figure 12:
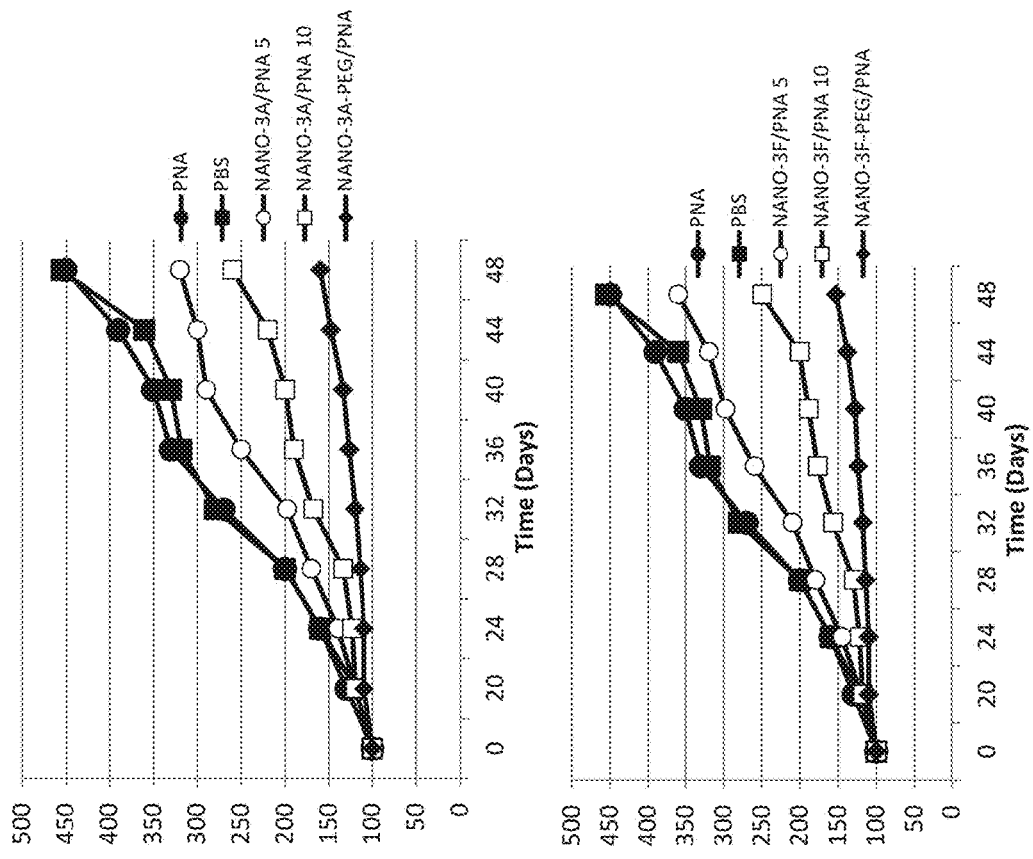

FIG. 12 shows reduction of tumor growth by intravenous administration of NANOPEP particles containing antisense PNA targeting Cyclin B1 in SKB3-HEK2 xenograft mice. NANO-3A/PNA 5: VEPEP-3a/PNA core (5 µg PNA), coated with VEPEP-3a; NANO-3A/PNA 10: VEPEP-3a/PNA core (10 µg PNA), coated with VEPEP-3a; NANO-3A-PEG/PNA: VEPEP-3a/PNA core, coated with PEG-VEPEP-3a; NANO-3F/PNA 5: VEPEP-3f/PNA core (5 µg PNA), coated with VEPEP-3f; NANO-3F/PNA 10: VEPEP-3f/PNA core (10 µg PNA), coated with VEPEP-3f; NANO-3F-PEG/PNA: VEPEP-3f/PNA core, coated with PEG-VEPEP-3f.

Figure 13:
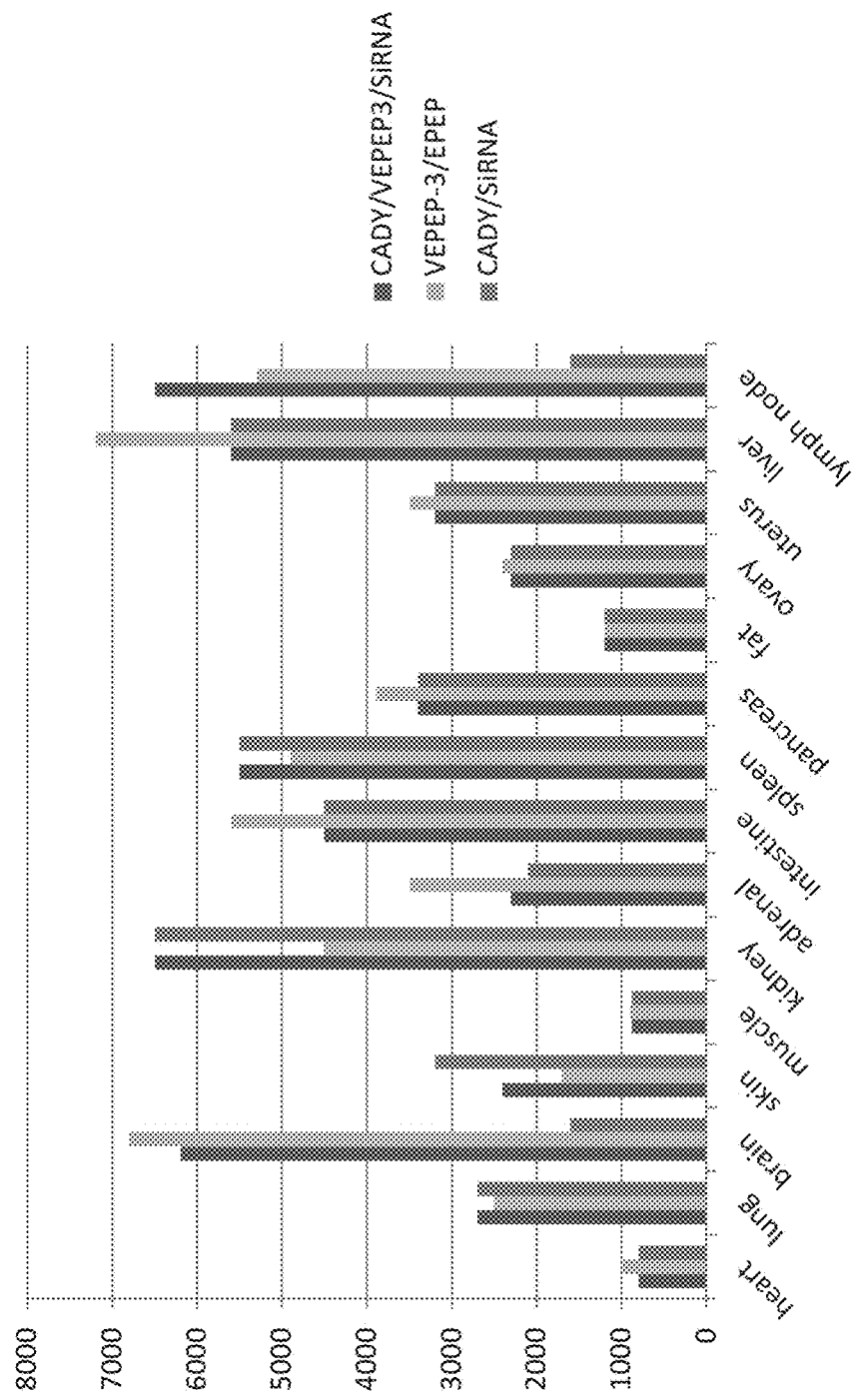

FIG. 13 shows in vivo biodistribution of fluorescently labeled peptide or siRNA delivered by intravenous administration of VEPEP-3 NANOPEP particles (as determined by live fluorescence animal imaging). CADY/VEPEP3/siRNA: CADY/siRNA core, coated with VEPEP-3; VEPEP-3/PEP: VEPEP-3/peptide core, coated with VEPEP-3; CADY/siRNA: CADY complexed with siRNA.

FIGS. 14A-14D show in vivo biodistribution of fluorescently labeled peptide or protein delivered by intravenous, intrarectal, intranasal or transdermal administration of VEPEP-3 NANOPEP particles (as determined by live fluorescence animal imaging). FIG. 14A shows results for intravenous administration. FIG. 14B shows results for intrarectal administration. FIG. 14C shows results for intranasal administration. FIG. 14D shows results for transdermal administration. VEPEP-3/PROT: VEPEP-3/protein core, coated with VEPEP-3; VEPEP-3/PEP: VEPEP-3/peptide core, coated with VEPEP-3.

DETAILED DESCRIPTION

The inventors have now designed a new family of cell-penetrating peptides for the delivery of peptides/proteins and hydrophobic molecules, named VEPEP-3. Delivery strategies using VEPEP-3 peptides as the outer layer of nanoparticles are referred to as NANOPEP-3.

VEPEP-3 are short primary amphipathic peptides forming stable nanoparticles with molecules such as peptide, protein, peptide-analogue, PNA and small hydrophobic molecules, hereafter designated as "SHM". VEPEP-3 vectors comprise the following amino acid sequence: $X_3X_4X_1X_2X_5X_4X_1X_2X_6X_7X_1X_8X_9X_{10}X_{11}X_{12}X_{13}$ (SEQ ID No: 11), wherein:

$X_1$ is F or W (independently from each other);
$X_2$ is F, W or Y (independently from each other);
$X_3$ is beta-A or S;
$X_4$ is K, R or L (independently from each other);
$X_5$ is E, R or S;
$X_6$ is R, T or S;
$X_7$ is E, R or S;
$X_8$ is none, F or W;
$X_9$ is P or R;
$X_{10}$ is R or L;
$X_{11}$ is K, W or R;
$X_{12}$ is R or F; and
$X_{13}$ is R or K.

According to a particular embodiment, this cell-penetrating peptide comprises an amino acid sequence $X_3X_1WX_2EX_1WX_2X_4X_5X_6PRX_1RX_1$ (SEQ ID No: 12), wherein:

$X_1$ is R or K (independently from each other);
$X_2$ is F, W or Y (independently from each other);
$X_3$ is beta-A or S;
$X_4$ is T or R;
$X_5$ is E or R; and
$X_6$ is W or F.

Non-limitative examples of cell-penetrating peptides according to the above paragraph comprise an amino acid sequence selected from the group consisting of:

$X_1$KWFERWFREWPRKRR (SEQ ID No: 1)

$X_1$KWWERWWREWPRKRK (SEQ ID No: 2)

$X_1$RWWEKWWTRWPRKRK, (SEQ ID No: 3)
and $X_1$RWYEKWYTEFPRRRR, (SEQ ID No: 4)

wherein $X_1$ is beta-A or S.

According to another particular embodiment of the present invention, the cell-penetrating peptide comprises the following amino acid sequence:

$X_3X_4X_1WX_2X_5X_1WX_2X_2WX_1X_6X_7WX_8R$, (SEQ ID No: 13)

wherein
- $X_1$ is F or W (independently from each other);
- $X_2$ is R or S (independently from each other);
- $X_3$ is beta-A or S;
- $X_4$ is K, R or L;
- $X_5$ is L or R;
- $X_6$ is R or P;
- $X_7$ is L or R; and
- $X_8$ is R or F.

According to a particular embodiment of the above cell-penetrating peptide, $X_8$ is R.

Non-limitative examples of cell-penetrating peptides according to the above paragraphs comprise an amino acid sequence selected from the group consisting of:

$X_1$RWWRLWWRSWFRLWRR (SEQ ID No: 5)

$X_1$LWWRRWWSRWWPRWRR (SEQ ID No: 6)

$X_1$LWWSRWWRSWFRLWFR, (SEQ ID No: 7)
and $X_1$KFWSRFWRSWFRLWRR, (SEQ ID No: 8)

wherein $X_1$ is beta-A or S.

The present invention also pertains to a stapled cell-penetrating peptide derived from a VEPEP-3 cell-penetrating peptide as described above. A "stapled" peptide designates a peptide which comprises a chemical linkage (in addition to the amino acid chain) between two residues. In a particular embodiment of stapled VEPEP-3 peptides, the VEPEP-3 peptide comprises a hydrocarbon linkage between two residues which are separated by three or six residues. The skilled artisan can obtain these peptides by using techniques which are available in the art, for example as described by Verdine and Hilinski, Methods in Enzymology, 2012 [12].

A particular embodiment of stapled VEPEP-3 according to the present invention comprises an amino acid sequence derived from SEQ ID No: 12 by addition of a non-natural amino acid between the amino acids in positions 2 and 3 of said sequence, replacement of the amino acid in position 9 of SEQ ID No: 12 by a non-natural amino acid, and addition of a hydrocarbon linkage between these two non-natural amino acids. An example of such a stapled VEPEP-3 CPP comprises the amino acid sequence $X_1KX_2$WWERWWRX$_3$WPRKRK (SEQ ID No: 9), wherein $X_1$ is a beta-alanine or a serine and wherein $X_2$ and $X_3$ are non-natural amino acids used for the binding of a hydrocarbon linkage.

Another embodiment of stapled VEPEP-3 according to the present invention comprises an amino acid sequence designed by replacement of the amino acids in position 5 and 12 of SEQ ID No: 13 by non-natural amino acids, and addition of a hydrocarbon linkage between the two non-natural amino acids (it being understood that the synthesis process directly integrates the non-natural amino acids). For example, a stapled VEPEP-3 peptide comprises the amino acid sequence $X_1RWWX_2LWWRSWX_3RLWRR$ (SEQ ID No: 10), wherein $X_1$ is a beta-alanine or a serine, and wherein $X_2$ and $X_3$ are non-natural amino acids used for the binding of a hydrocarbon linkage.

VEPEP-3 strategy improves both ex-vivo and in vivo delivery and efficiency of peptide/protein/peptide analogue and small hydrophobic molecules, without activating the innate immune response or inducing toxic side effects.

According to a preferred embodiment, a cell-penetrating peptide of the present invention further comprises, covalently linked to the N-terminal end of the amino acid sequence, one or several chemical entities selected in the group consisting of an acetyl, a fatty acid, a cholesterol, a poly-ethylene glycol, a nuclear localization signal, a nuclear export signal, an antibody, a polysaccharide and a targeting molecule (peptide, fatty acid, saccharide).

As developed below and shown at least in example 5 below, PEGylation of VEPEP-3 peptides is particularly advantageous for stabilizing nanoparticles in vivo.

In addition or alternatively, a cell-penetrating peptide according to the invention can comprise, covalently linked to the C-terminal end of its amino acid sequence, one or several groups selected in the group consisting of a cysteamide, a cysteine, a thiol, an amide, a nitrilotriacetic acid optionally substituted, a carboxyl, a linear or ramified C1-C6 alkyl optionally substituted, a primary or secondary amine, an osidic derivative, a lipid, a phospholipid, a fatty acid, a cholesterol, a poly-ethylene glycol, a nuclear localization signal, nuclear export signal, an antibody, a polysaccharide and a targeting molecule.

Another aspect of the present invention is a complex comprising a cell-penetrating peptide as described above and a cargo selected amongst protein/peptide and hydrophobic molecules. Examples of polypeptide cargoes are small peptide or protein, cyclic peptide, peptide-based biomarker, bio-drug, PNA or uncharged oligonucleotides. In a preferred embodiment of the complex according to the invention, the cargo is a small molecule (size lower than 1.5 kDa), either hydrophobic or charged. Preferred cargos in the complexes according to the present invention are anticancer and antiviral drugs. Non-limitative examples of small hydrophobic molecules which can be used include amino acids, di- or tri-peptides (labelled or not) daunomycin, Paclitaxel, doxorubicin, AZT, porphyrin, fluorescently-labelled-nucleosides or nucleotides (FAM-Guanosine, CY5_UTP, CY3-UTP), hydrophobic maghemite (contrast agents or magnetic nanoparticles $Fe_2O_3$) and fluorescent dyes.

The size of the complexes described above is preferably between 50 and 300 nm, more preferably between 50 and 200 nm (the size of the complex herein designates its mean diameter).

In the complexes according to the invention, the cargo/VEPEP-3 molar ratio depends on the nature and size of the cargo, but is generally comprised between 1/1 and 1/50. For small peptide cargoes, the cargo/VEPEP-3 molar ratio preferably ranges from 1/5 to 1/20. For small molecule cargoes, the cargo/VEPEP-3 molar ratio preferably ranges from 1/3 to 1/10. For large protein cargoes, the cargo/VEPEP-3 molar ratio preferably ranges from 1/10 to 1/40.

According to an advantageous embodiment of the complexes as described above, the VEPEP-3 peptides comprise a polyethylene glycol group or an acetyl group covalently linked to their N-terminus, and/or a cysteamide group covalently linked to their C-terminus.

The above complexes can be advantageously used as "core shells" for obtaining bigger complexes, or nanoparticles, by an additional step of coating the cargo/VEPEP-3 complex with another layer of cell-penetrating peptides, which can be different from the VEPEP-3 peptides described above. Examples of such nanoparticles are VEPEP-3/CADY (wherein CADY is a CPP as described in EP1795539 and in [11], for example CADY-1: Ac-GLWRALWRLLRSLWRLLWKA-cysteamide (SEQ ID No: 28)), VEPEP-3/PEP-1 (wherein Pep-1 is a CPP as described in [8]), VEPEP-3/MPG (wherein MPG is a CPP as described in U.S. Pat. No. 7,514,530 and in [7, 10]), as well as nanoparticles with an outer layer made of a CPP belonging to another VEPEP family, for example selected from the following list:

VEPEP-6a: (SEQ ID No: 29)
Ac-$X_1$LFRALWRLLRSLWRLLWK-cysteamide

VEPEP-6b: (SEQ ID No: 30)
Ac-$X_1$LWRALWRLWRSLWRLLWKA-cysteamide

VEPEP-6c: (SEQ ID No: 31)
Ac-$X_1$LWRALWRLLRSLWRLWRKA-cysteamide

VEPEP-6d: (SEQ ID No: 32)
Ac-$X_1$LWRALWRLWRSLWRLWRKA-cysteamide

VEPEP-6e: (SEQ ID No: 33)
Ac-$X_1$LWRALWRLLRALWRLLWKA-cysteamide

VEPEP-6f: (SEQ ID No: 34)
Ac-$X_1$LWRALWRLLRNLWRLLWKA-cysteamide

VEPEP-9a1: (SEQ ID No: 35)
Ac-$X_1$LRWWLRWASRWFSRWAWWR-cysteamide

VEPEP-9a2: (SEQ ID No: 36)
Ac-$X_1$LRWWLRWASRWASRWAWFR-cysteamide

VEPEP-9b1: (SEQ ID No: 37)
Ac-$X_1$RWWLRWASRWALSWRWWR-cysteamide

VEPEP-9b2: (SEQ ID No: 38)
Ac-$X_1$RWWLRWASRWFLSWRWWR-cysteamide

VEPEP-9c1: (SEQ ID No: 39)
Ac-$X_1$RWWLRWAPRWFPSWRWWR-cysteamide

VEPEP-9c2: (SEQ ID No: 40)
Ac-$X_1$RWWLRWASRWAPSWRWWR-cysteamide

VEPEP-9d: (SEQ ID No: 41)
Ac-$X_1$WWRWWASWARSWWR-cysteamide

VEPEP-9e: (SEQ ID No: 42)
Ac-$X_1$WWGSWATPRRRWWR-cysteamide

VEPEP-9f: (SEQ ID No: 43)
Ac-$X_1$WWRWWAPWARSWWR-cysteamide

ST-VEPEP-6a: (SEQ ID No: 44)
Ac-$X_1$LFRALW$R_S$LLR$S_S$LWRLLWK-cysteamide

-continued

ST-VEPEP-6aa: (SEQ ID No: 45)
Ac-$X_1$LFLARW$R_S$LLR$S_S$LWRLLWK-cysteamide

ST-VEPEP-6ab: (SEQ ID No: 46)
Ac-$X_1$LFRALW$S_S$LLR$S_S$LWRLLWK-cysteamide

ST-VEPEP-6ad: (SEQ ID No: 47)
Ac-$X_1$LFLARW$S_S$LLR$S_S$LWRLLWK-cysteamide

ST-VEPEP-6b: (SEQ ID No: 48)
Ac-$X_1$LFRALWRLL$R_S$SLW$S_S$LLWK-cysteamide

ST-VEPEP-6ba: (SEQ ID No: 49)
Ac-$X_1$LFLARWRLL$R_S$SLW$S_S$LLWK-cysteamide

ST-VEPEP-6bb: (SEQ ID No: 50)
Ac-$X_1$LFRALWRLL$S_S$SLW$S_S$LLWK-cysteamide

ST-VEPEP-6bd: (SEQ ID No: 51)
Ac-$X_1$LFLARWRLL$S_S$SLW$S_S$LLWK-cysteamide

ST-VEPEP-6c: (SEQ ID No: 52)
Ac-$X_1$LFA$R_S$LWRLLR$S_S$LWRLLWK-cysteamide, as well as variants thereof (regarding the amino acid sequence and/or the N- and C-terminal chemical groups), wherein $X_1$ is beta-A or S and wherein the residues followed by an inferior "s" are linked by a hydrocarbon linkage. Preferred variants of the above sequences for forming nanoparticles according to the invention are PEGylated at their N-terminal extremity instead of being acetylated.

Another aspect of the present invention pertains to nanoparticles made of a "core shell" comprising a cargo and a first carrier molecule, surrounded by VEPEP-3 peptides. These are herein referred to as "NANOPEP-3" particles. NANOPEP-3 technology constitutes a "custom-built" delivery system containing a common core particle, trapping therapeutic molecule, with surface VEPEP-3 peptides which are preferably functionalized for tumour or tissue targeting in vivo. From a structural point of view, NANOPEP-3 particles are constituted by a "core" which is coated by a layer of VEPEP-3 peptides. The "core" corresponds to a complex comprising a cargo and a vector or carrier such as a first cell-penetrating peptide, a liposome, a polycationic structure, a carbon nanoparticle, etc. In NANOPEP-3 particles, the layer of VEPEP-3 peptides (peripheral peptide) stabilizes the particle and can be functionalized. Functionalizing NANOPEP-3 particle surface with either cholesterol, lipid, PEG-molecules improves particles stability in vivo, favours their administration by either systemic or topical route and allows rapid liberation of active cargoes within tumor cells or tissues. Functionalization of the surface of NANOPEP-3 particles with small FAB fragments, peptides, antibodies and lipids has been shown to favour in vivo tissue or tumor targeting. Also, Functionalizing NANOPEP-3 particle surface with polysaccharide such as PLGA, can be used as formulation for slow release of drug and cargo and allow a long term response in vivo. As shown in Example 5 below, the inventors have observed that N-terminal PEGylation of at least part of the VEPEP-3 peptides surrounding the NANOPEP-3 particles increases the biodistribution of cargoes in the tumour, probably by stabilizing the NANOPEP-3 particles in the plasma.

NANOPEP-3 technology improves both cellular and in vivo delivery of biologically active cargoes and has been validated on a large set of cell lines including adherent and suspension cell lines, hard to transfect cell lines. NANO- PEP-3 particles strongly interact with cell membranes and enter the cell independently of the endosomal pathway or rapidly escape from early endosomes. NANOPEP-3 technology presents several advantages including rapid delivery with very high efficiency, stability in physiological buffers, protection of the cargo against degradation, lack of toxicity and of sensitivity to serum, ability of forming mix nanoparticles, can be functionalized and have been successfully applied to the delivery of different types of cargoes into a large variety of cell lines as well as in animal models, thereby constituting powerful tools for basic research and therapeutic applications. NANOPEP-3 technology can be applied both at therapeutic and diagnostic/theragnostic levels, as well as for imaging, for example brain imaging.

In a particular embodiment of NANOPEP-3 particles according to the present invention, the cargo is complexed to a first cell-penetrating peptide, which can be, for example, selected amongst CADY, MPG, PEP-1, PPTG1, poly Arginine motif, VEPEP-family peptide (VEPEP-3, VEPEP-6, VEPEP-9, stapled or not) as described above (such as SEQ ID Nos: 1 to 13 and 19 to 52 and variants thereof), or any other known CPP. This cargo/CPP complex is then coated with a layer of VEPEP-3 peptides. According to this embodiment, the skilled artisan will advantageously choose the first CPP depending on the nature of the cargo, so that the complex of cargo and first CPP is stable. Hence, a wide diversity of cargoes can be included in NANOPEP-3 particles.

In the nanoparticles as above-described, the core/VEPEP-3 molar ratio depends on the nature and size of the core, but is generally comprised between 1/1 and 1/50. For small peptide/CPP cores, the core/peripheral VEPEP-3 molar ratio preferably ranges from 1/5 to 1/30, depending on the nature of peptide cargo (hydrophobicity and charge).

In a preferred embodiment of the nanoparticles according to the invention, the size of the nanoparticle is between 20 and 300 nm.

According to an advantageous embodiment of the NANOPEP-3 particles according to the invention, the VEPEP-3 peptides forming the peripheral layer of the nanoparticles comprise a poly-ethylene glycol or an acetyl group covalently linked to their N-terminus, and/or a cysteamide group covalently linked to their C-terminus.

According to another preferred embodiment, the core shell of the particles is coated with a VEPEP-3 peptide functionalized with NTA (for example, a VEPEP-3 peptide with nitrilotriacetic acid covalently linked to its C-terminus). This allows the subsequent attachment to the surface of the particle, of any protein (or other molecule) harboring a histidine tag. This strategy offers the major advantage of having a common two-layers particles "NANOPEPHIS-3" which can be associated to any His-tagged molecule.

In particular embodiments of the complexes and nanoparticles according to the invention, at least part of the VEPEP-3 cell-penetrating peptides are bound to a targeting molecule. In the case of NANOPEP-3 particles, at least part of the cell-penetrating peptides which are at the periphery of the nanoparticle are preferentially bound to a targeting molecule. Examples of targeting molecules include antibodies, nanobodies and Fc or FAB fragments (for example targeting HEK2/MUC1/EGF/XCCR4), ligands, especially targeting receptors which are over-expressed at the surface of certain cell-types and homing peptides specific of selected organs. Non-limitative examples of such ligands and homing peptides are: RGD-peptide, homing targeting peptides (brain NT1 peptide, Ganglion GM1 peptide, as well as all other previously described peptides for tissues and cell line targeting), folic acid, polysaccharides, and matrix metalloprotease targeting peptide motif (MMP-9 or MMP3 for tumour selectivity).

According to a particular embodiment of the present invention, the complexes or nanoparticles are formulated se that they can be stored during several months without losing their stability and functional efficacy. As disclosed in example 5 below, the complexes and nanoparticles of the invention can advantageously be lyophilized in the presence of a sugar. Non-limitative examples of sugars which can be used to that aim are sucrose, glucose, manitol and a mix thereof, and they can be used, for example, in a concentration ranging from 5% to 20%, preferably 5% to 10%, it being understood that a concentration of 5% is obtained by adding 5 grams per liter of solution before lyophilization.

Another aspect of the present invention is the use of a complex or nanoparticle as above-described, as a medicament and as a marker or an imaging agent.

In particular, the VEPEP-3/cargo complexes and NANOPEP-3 particles can advantageously be used in the treatment of a brain disease and/or of a lymph node disease, for example by targeting a latency pathogen localized in the brain and/or in a lymph node. They can also be used for brain and/or lymph node imaging.

The present invention also pertains to a therapeutic, cosmetic or diagnostic composition comprising a complex or a nanoparticle as described above. For example, a composition comprising a complex or nanoparticle having a peptide targeting protein/protein interactions, involving essential protein CDK and Cyclin required for cell cycle progression as a cargo, and a targeting molecule specific for tumour cells (for example: RGD-peptide, folic acid, MUC-1 or HEK2 antibodies or nanobodies), is part of the present invention. Depending on the application, this composition can be formulated for intravenous, intratumoral, topical, intrarectal, intranasal, transdermal, or intradermal administration, or for administration via a mouth spray, or for administration as a subcutaneous implant for slow release of a drug.

The present invention also pertains to a method for delivering a molecule into a cell in vitro, comprising a step of putting said cell into contact with a complex or nanoparticle as described above.

Several aspects of the present invention are further developed in the following examples, illustrated by the figures (which are described in the examples).

Example 1: Materials and Methods

VEPEP-3 Peptides

All peptides were synthesized by solid-phase peptide synthesis using AEDI-expensin resin with (fluorenylmethoxy)-carbonyl (Fmoc) on a Pioneer Peptide Synthesizer (Pioneer™, Applied Biosystems, Foster City, Calif.) starting from Fmoc-PAL-PEG-PS resin at a 0.2 mmol scale. The coupling reactions were performed with 0.5 M of (HATU in the presence of 1 M of DIEA. Protecting group removal and final cleavage from the resin were carried out with TFA/Phenol/$H_2O$/Thioanisol/Ethanedithiol (82.5/5/5/5/2.5%) for 3 h 30 min. All the peptides presented a cysteamide group at the C-terminus and were acetylated at the N-terminus. The peptide synthesis started by the C-terminus, using an AEDI-expensin resin starting with a cysteamide link, as described by Mery et al., 1992 [9]. All the peptides contained a beta-Alanine or a serine at the N-terminus to favour any further functionalization without using the C-terminal cysteamide group.

Functionalization of Vepep-3

Two approaches were used for peptide functionalization (1) Peptide conjugations with peptide, antibody, pegylation, NTA, cholesterol, stearylation, were performed at the primary amino group of the N-terminal residue, through a beta alanine or serine. It is advantageous to maintain the C-terminal cysteamide free, since it is known to be required to stabilize the particle through disulfide bounds (SH-SH).

Functionalized peptides were further purified by Reverse Phase-HPLC and analyzed by electro-spray ionization mass spectroscopy.

(2) Peptide conjugations were also performed via disulfide bound using the SH-group of the cysteamide moiety of the peptide.

VEPEP-3-Funct-1:
(SEQ ID No: 14)
X-LWWRRWWSRWWPRWRR-CH$_2$-CH$_2$-SH

VEPEP-3-Funct-2:
(SEQ ID No: 15)
Ac-LWWRRWWSRWWPRWRR-CH$_2$-CH$_2$-S-S-X

VEPEP-3-Funct-3:
(SEQ ID No: 16)
X-W(W-F)RLW(W-F)RLR-CH$_2$-CH$_2$-SH

VEPEP-3-Funct-4:
(SEQ ID No: 17)
Ac-W(W-F)RLW(W-F)RLR-CH$_2$-CH$_2$-S-S-X

X: Cholesterol, Pegylation, stearyl, palmitoyl, small FC or FAB fragments, nanobody, nitrilotriacetic acid (2×NTA), tissue-targeting peptides (brain, lung, lymph node, pancreas . . . ).

VEPEP-3 Structure

VEPEP-3 peptides are primary amphipathic peptides; they are highly versatile and show a strong structural polymorphism. VEPEP-3 peptides are unfolded in solution as a free form and adopt an alpha helical conformation in the N-terminal part in the presence of lipid or artificial cellular membranes as well as in the presence of cargos such as peptide or protein.

Peptides and Proteins

Peptides targeting CDK/Cyclin (C4, C2 sequences of SEQ ID Nos: 20 to 23) or HIV integrase (PC4 & PC6 sequences of SEQ ID Nos: 24 to 27) linear or cyclic version were obtained for Polypeptide.

C2:
(SEQ ID No: 20)
KKQVLAMEHLVT

C2S:
(SEQ ID No: 21)
VTLMEAKKQVLT

C4:
(SEQ ID No: 22)
KKQVRMAHLVLT

C4C:
(SEQ ID No: 23)
CKKQVRMAHLVLTC

PC4, also noted PC4D
(SEQ ID No: 24)
RWTEWEWW

PC4S:
(SEQ ID No: 25)
TWFTEWFT

PC6, also noted PC6D:
(SEQ ID No: 26)
KWETWWET

PC6S:
(SEQ ID No: 27)
KAETWAET

Proteins; including GFP overexpressed in *E. coli* and short protein nanobodies, corresponding to chamelidea antibodies were also expressed in *E. coli*.

Oligonucleotides & PNA

Short oligonucleotides, PNA and 5' Alexa$^{700}$ or Cy5 fluorescently labelled PNA were synthesized by Eurogentec (Belgium) according to the following sequences:

Cyc-Bla;
(SEQ ID No: 18)
TGC CAT CGG GCT TGG AGG-$^{Cy5}$

Cyc-Bct;
(SEQ ID No: 19)
TGC CAT CAA GCT TAG AGG-$^{Cy5}$

Fluorescence Titrations

Fluorescence experiments were performed on a PTI spectrofluorimeter at 25° C. in a NaCl 154 mM buffer. Intrinsic Trp-fluorescence of VEPEP-3 was excited at 290 nm and emission spectrum was recorded between 310 and 400 nm, with a spectral band-pass of 2 and 8 nm for excitation and emission, respectively. FITC-fluorescence of labelled-peptide was excited at 492 nm and emission recorded between 500 and 580 nm. For VEPEP-3/peptide interaction, 0.5 µM of FITC-labelled peptide was titrated by increasing concentrations of VEPEP-3. All measurements were corrected for the dilution and curve fitting were performed by using Grafit software (Erithacus).

Characterization of Peptide-Based Nanoparticles

Mean particle size distribution was determined with a Coulter N4 Plus (Coulter-Beckman) at 25° C. for 3 min per measurement and zeta potential was measured with Zetasizer 4 apparatus (Malvern Ltd)

Cell Culture and VEPEP-Mediated Cargo Delivery

Adherent HS68 fibroblasts, HeLa, PC3, MCF-7, SCK3-Her2, PBMC cell lines (from American Type Culture Collection (ATCC)) were cultured in Dulbecco's Modified Eagle's Medium supplemented with 2 mM glutamine, 1% antibiotics (streptomycin 10,000 µg/ml, penicillin, 10,000 IU/ml) and 10% (w/v) foetal calf serum (FCS), at 37° C. in a humidified atmosphere containing 5% CO$_2$. Stock solutions of VEPEP-3/peptide particles were prepared by complexing 1 µM peptide with VEPEP-3 peptides at a molar ratio of 1/20 for 30 min at 37° C. Lower concentrations of VEPEP-3-carrier/peptide (from 500 nM to 1 µM) were obtained by serial dilution of the stock complexes in PBS, in order to preserve the same VEPEP-3-carrier/peptide ratio. 150,000 cells seeded in a 35 mm dish the day prior transfection, were grown to 60% confluence and overlaid with 200 µl of preformed complexes, incubated for 3-5 min, then 400 µl of DMEM were added. After 30 min incubation at 37° C., 1 ml of fresh DMEM containing 16% foetal calf serum (FCS) was added in order to reach a final FCS concentration of 10%, without removing the overlay of VEPEP-3/peptide complexes. Cells were returned to the incubator for 24 hrs. For cdk4 and CDK2 derived peptides cell proliferation was monitored after 24 and 48 hrs. For peptide-targeting integrase, HIV proliferation was analyzed on activated PBMC cells after 3 and 5 days. Data reported are an average of 3 or 4 distinct experiments.

Cytotoxicity

Toxicity of VEPEP-3/peptide or VEPEP-3/protein complexes was investigated on Hela and HS-68 cell lines. 30,000 cells seeded in 24-well plated the day prior transfection, were incubated with increasing concentrations of peptide or protein complexed with VEPEP-3 at a 20/1 molar ratio ranging from 1 to 5 µM (500 µM VEPEP-3), for 30 min. prior to addition of medium to reach a final 10% concentration of FCS. Cytotoxic response was measured 12 hr or 24 hr later by monitoring the housekeeping gene cyclophilin mRNA level (Quantigen, Panomic Inc.) and by colorimetric MTT assay (Sigma, Germany), respectively. For MTT assay, cell culture medium was removed and replaced with PBS containing 2.5 mg/ml of MTT for 4 hr. Results correspond to the average of 3 separate experiments.

Mouse Tumour Models

Athymic female nude mice (6-8 weeks of age) were subcutaneously inoculated into the flank with $1\times10^6$ PC3, A549 or SCK-3-HEK2 cells in 100 µl PBS. Two to three weeks after tumour implant, when tumour size reached about 100 mm$^3$, animals were treated by intratumoral or intravenous injection, every 3 days, with a solution of 0.1 ml of either free CDK2 or CDK4 derived peptide (200 µg), control scramble peptide C4C or C4 or C2 peptides (10, 50, 100 µg) complexed with NANOPEP-3 at a 1/20 molar ratio. Tumour diameter was measured in two directions at regular intervals using a digital calliper and tumour volume was calculated as length×width×height×0.52. Curves show the mean value of tumour size in a cohort of six animals and neither animal death nor any sign of toxicity were observed.

Experiments were performed according to national regulations and approved by the local animal experimentation ethical committee. The statistical significance of the results was calculated by Student's t test and p<0.05 considered to be statistically significant.

In Vivo Imaging of Peptide Biodistribution

In vivo fluorescence imaging was performed as previously described by Crombez et al, 2009, Nucleic Acid Res [10]. Mice were injected intravenously with 100 µg (200 µl) of Alexa700 fluorescently labelled peptide (C4) either naked or complexed with VEPEP-3 (n=4 animals per group). Anaesthetized mice, using 2% Isoflurane, were illuminated by 663 nm light emitting diodes equipped with interference filters and movies were acquired over the first 15 minutes and fluorescence images were taken every hour for 5 hrs and then after 24 hrs, with a back-thinned CCD cooled camera as previously described (Crombez et al, 2009, Nucleic Acid Res). At 24 hr mice were euthanized and different organs were removed for quantification of Alexa fluorescence.

Example 2: VEPEP-3 Peptides Applications for Molecules Delivery

Example 2.1: VEPEP-3 Peptides Form Stable Nanostructures with Peptides and Proteins VEPEP-3 peptide form stable complexes with peptides and proteins. The binding of cargos to VEPEP-3 was monitored by fluorescence spectroscopy using the two intrinsic Trp groups of VEPEP-3 (3 to 5 Trp-residues) and extrinsic fluorescently labelled cargoes (using Cy3, Cy5 or FITC). Curve fitting reveal that VEPEP-3 strongly binds the different cargoes with dissociation constant in the nanomolar range (examples with VEPEP-3a, VEPEP-3C, and VEPEP-3g and three different cargoes are reported in FIG. 1, all the data are reported in Table 1).

Example 2.2: VEPEP-3 Peptides Form Stable Nanostructures with Small Hydrophobic Molecules VEPEP-3 peptides also form stable particles with small aromatic molecules including Daunomycin, Paclitaxel, doxorubicin, porphyrin and charged molecules including nucleotide, nucleoside and peptide-analog of nucleic acids or fluorescent dyes (FIG. 1). The dissociation constant for small hydrophobic molecule ranges between 0.05 to 2 µM, depending on the nature of the dyes and of the peptides.

TABLE 1

VEPEP-3/Cargo complexes characterization. Peptide (C4 and C2), Cyclic peptide (PC4), protein (GFP & Nanobody), SHM: Doxorubicine small hydrophobic molecule and PNA (15 mer -PNA).

| VEPEP-3 | SEQ ID No | Cargoes | | | | | | | | | |
|---|---|---|---|---|---|---|---|---|---|---|---|
| | | peptide | | Cyclic peptide | | Protein | | SHM | | PNA | |
| | | Binding | Kd (nM) | Binding | Kd (nM) | Binding | Kd (µM) | Binding | Kd (µM) | Binding | Kd (nM) |
| VEPEP-3a | 1 | yes | 10-20 | yes | 50-100 | Yes | 1 | Yes | 1 | Yes | 100 |
| VEPEP-3b | 2 | yes | 10-20 | yes | 50-100 | Yes | 0.5 | Yes | 0.5 | Yes | 200 |
| VEPEP-3c | 3 | yes | 10-20 | yes | 50-100 | Yes | 0.2 | Yes | 0.2 | Yes | 200 |
| VEPEP-3d | 4 | yes | 10-20 | yes | 50-100 | Yes | 0.1 | Yes | 0.1 | Yes | 100 |
| VEPEP-3e | 5 | yes | 10-20 | yes | 5-20 | Yes | 0.02-0.1 | Yes | 0.02 | Yes | 5-50 |
| VEPEP-3f | 6 | yes | 10-20 | yes | 5-20 | Yes | 0.02-0.1 | Yes | 0.02 | Yes | 5-50 |
| VEPEP-3g | 7 | yes | 10-20 | yes | 5-20 | Yes | 0.02-0.1 | Yes | 0.02 | Yes | 5-50 |

Figure 2:
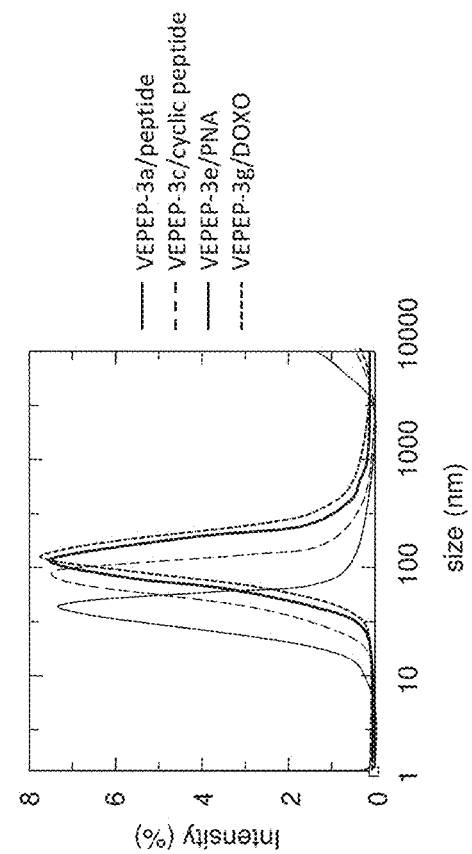
FIG. 2 shows the particle size distribution of several VEPEP-3/cargo complexes (VEPEP-3a/peptide, VEPEP-3c/ cyclic peptide, VEPEP-3e/PNA, and VEPEP-3g/Doxo) at molar ratios ranging between 1:10 and 1:30 (as determined by dynamic light scattering).

Example 2.3: VEPEP-3 Peptides Form Stable Nanoparticles with their Different Cargoes The size of the particles was monitored by dynamic light scattering. The optimal VEPEP-3 peptide/cargo molar ratio is ranging between 1/10 to 1/30, FIG. 2 reports DLS analysis of VEPEP-3a/peptide, VEPEP3c/cyclic peptide, VEPEP-3e/PNA and VEPEP-3g/Doxo particles formed at ratio 1/20 (FIG. 2). The size of the particles is of about 100 to 200 nanometers in diameter.

Example 3: VEPEP-3 Applications in Cultured Cells

Example 3.1: VEPEP-3 Mediated Delivery of Peptide and Cyclic Peptide in Different Cell Lines VEPEP-3 peptides have been used for the delivery of different peptides into different cell lines, including primary cell lines, stem cell lines and challenging cell lines. Peptide delivery was monitored using three approaches: fluorescence spectroscopy and monitoring of biological responses (anti proliferation and anti viral responses)

1—Fluorescent labelled peptide was visualized in the different cell lines using fluorescence microscopy or FACS sorting (Table 2). In most of the cell lines, the uptake of Cy-5 labelled peptides is more than 70% of the cells.

2—Dose-response experiments performed on different cultured cells revealed that VEPEP-3-mediated delivery of C2 and C4 peptides, targeting either cdk2/cyclin A or CDK4/cyclin D complexes, blocks cell proliferation of different cancer cells.

3—Dose-response experiments performed on HIV infected activated PBMC cells revealed that VEPEP-3-mediated delivery of PC4D peptides, targeting pre-integration complex and HIV integrase, blocks viral replication (the effect of PC4D in complex with VEPEP-3a, VEPEP-3c and VEPEP-3g is shown on FIG. 3).

TABLE 2

| Cell lines | origin | Efficiency FACS analysis of Cy-5 C4 |
|---|---|---|
| Hela | Human epithelial cervical cancer cells | 75% |
| Jurkat | Human T lymphocyte | 90% |
| HepG2 | Human hepatocyte | 70% |
| C2C12 | Mouse myoblast | 90% |
| MEF | Mouse fibroblast | 90% |
| HS-68 | Human fibroblast | 90% |
| CEM-SS | Human macrophage | 80% |
| U2OS | Human osteoblast | 91% |
| MCF7 | Human breast adenocarcinoma | 70% |
| MT4 | Human T lymphocyte | 70% |
| HER2 | Human breast cancer | 90% |
| MDA-MB | Human breast cancer | 70% |
| PBMC | Human macrophage | 90% |

Example 3.2: VEPEP3-Mediated Delivery of Peptide Targeting Cdk2/Cyclin A or CDK4/Cyclin D Induces G2 Arrest & Blocks Cancer Cell Proliferation Dose-response experiments performed on cultured cells revealed that VEPEP-3 mediated delivery of C2 and C4 peptide induced a robust biological response associated with specific cell cycle arrest in G2 (FIG. 4). A peptide C2 or C4 concentration of 200 nM was sufficient to block proliferation of Hela, MCF7, HEK-2, HS-68 and U2OS cells. $IC_{50}$ of 35±12 nM and 37±15 nM were estimated for C4 and C2 peptides, respectively on Hela, of 58±6 nM and 67±15 for C4 and C2 peptides, respectively on MCF7, and of 78±10 nM and 102±24 nM for C4 and C2 peptides, respectively, on HEK-2. In contrast, proliferation was only reduced by 10 to 20% for non-transformed HS68 fibroblasts, in perfect agreement with the impact of the check point G2-M on the cell cycle proliferation and showing the specificity of the peptide for cancer cells. FIG. 5 shows an example with VEPEP-3a, VEPEP-3d and VEPEP-3g.

C2 and C4 mediated dissociation of CDK2/cyclin A or CDK4/cyclin D complex was directly associated with accumulation of cells with a 4N content, consistent with down-regulation of Cdk1-Cyclin B1 activity, and was optimally obtained with 200 nM peptide and $IC_{50}$ values estimated to 36±21 nM and 46±14 nM for HeLa and MDA_MB cells, respectively (FIG. 5). FIG. 4 shows an example using VEPEP-3a with C2 and C4 at molar ratio 1/20. In contrast, no effect on cell cycle progression was observed with 500 nM of a scrambled C2 peptides complexed with VEPEP-3a at a 20/1 ratio, or with VEPEP-3a carrier alone (200 µM).

Example 3.3: VEPEP3-Mediated Delivery of Peptide Targeting HIV Integrase Blocks HIV Virus Replication The anti-HIV activities of the peptides (PC4D, PC6D & PC4S) and VEPEP-3/peptides were assayed according to previously described method (Roisin et al, 2004). Phytohemagglutinin-P (PHA-P)-activated peripheral blood mononuclear cells (PBMC) treated by increasing concentrations of peptide (from 100 to 0.1 nM), one hour later, were infected with hundred 50% tissue culture infectious doses ($TCID_{50}$) per 100,000 cells of the HIV-1-LAI or different resistant strains (Barre-Sinoussi et al, 1983). Viruses were amplified in vitro on PHA-P-activated PBMC. Viral stock was titrated using PHA-P-activated PBMC, and 50% $TCID_{50}$ were calculated using Kärber's formula (Karber 1931). Samples were maintained throughout the culture, and cell supernatants were collected at day 7 post-infection and stored at −20 C. Viral replication was measured by quantifying RT activity in cell culture supernatants. In parallel, cytotoxicity of the compounds was evaluated in uninfected PHA-P-activated PBMC by colorimetric 3-(4-5 dimethylthiazol-2-yl)2,5 diphenyl tetrazolium bromite (MTT) assay on day 7 (Mossmann 1983). Experiments were performed in triplicate and repeated with another blood donor. Data analyses were performed using SoftMax®Pro 4.6 microcomputer software: percent of inhibition of RT activity or of cell viability were plotted vs. concentration and fitted with quadratic curves; 50% effective doses ($ED_{50}$) and cytotoxic doses ($CD_{50}$) were calculated.

Dose-response experiments performed on cultured cells revealed that VEPEP-3a, VEPEP-3c and VEPEP-3g mediated delivery of PC4D and PC6D significantly blocks viral replication on PBMC infected by HIV-$1_{LAI}$ (FIG. 3). When associated to the carrier peptide VEPEP-3, PC4D and PC6D exhibit a 15-fold higher antiviral activity than AZT, which is the reference RT-inhibitor currently used in clinic: $IC_{50}$ of 0.12±0.05 nM and 0.09±0.05 nM, respectively. In contrast, the scrambled peptides PC4S and PC6S do not show any anti viral activity. Both VEPEP-3/peptide complexes do not induce a toxic response and have a selectivity index greater than 5400, which is 10-fold higher than that of AZT.

Example 3.4: VEPEP-3 Mediated Delivery of Proteins in Different Cell Lines

VEPEP-3 have been used for the delivery of different proteins into different cell lines, including primary cell lines, stem cell lines and challenging cell lines. Protein uptake was monitored using fluorescence spectroscopy and FACS analysis. GFP/RFP or Fluorescent labelled proteins were visualized in the different cell lines using fluorescence microscopy or FACS sorting (Table 3). In most of the cell lines, the uptake of RFP; GFP, Cy-5 labelled proteins is more than 70% of the cells.

TABLE 3

| Cell lines | origin | Efficiency GFP | Efficiency Cy-protein |
|---|---|---|---|
| Hela | Human epithelial cervical cancer cells | 67% | 90% |
| Jurkat | Human T lymphocyte | 80% | 90% |
| HepG2 | Human hepatocyte | 69% | 70% |
| C2C12 | Mouse myoblast | 80% | 90% |
| MEF | Mouse fibroblast | 75% | 90% |
| HS-68 | Human fibroblast | 80% | 90% |
| CEM-SS | Human macrophage | 80% | 80% |
| U2OS | Human osteoblast | 70% | 91% |
| MCF7 | Human breast adenocarcinoma | 65% | 70% |
| MT4 | Human T lymphocyte | 50% | 55% |

Example 3.5: VEPEP3-Mediated Delivery of Peptide and Protein is not Toxic

As shown on FIG. 6, the toxicity of VEPEP-3 particles was investigated on HeLa and U2OS cells by MTT assay and by monitoring the level of cyclophilin mRNA measured by Quantigen™ technology (Affymetrix). VEPEP-3a; VEPEP-3b, VEPEP-3c, VEPEP-3d, VEPEP-3e, VEPEP-3f, VEPEP-3g and VEPEP-3h were complexed with short peptide and PNA at ratio 1/20 No toxicity was detected at levels up to 200 nM, and only a mild toxicity was observed at the maximum concentration of 1 µM.

Example 3.6: VEPEP-3 Mediated Delivery of PNA Molecule in Different Cell Lines VEPEP-3 peptides have been used for the delivery of nucleic acid analogues (PNA and morpholino) into different cell lines, including primary cell lines and challenging cell lines. We demonstrated that VEPEP-3a and VEPEP-3h form stable complexes with small PNA or morpholino oligonucleotide of 15 mer. We have applied VEPEP-3 strategy for the delivery of PNA antisense targeting Cyclin B1 as previously described (Morris et al, 2007). Dose-response experiments performed on different cultured cells revealed that VEPEP-3-mediated delivery of PNA (Cyclin B1) induced a robust downregulation higher than 70% of Cyclin B1 protein level (FIG. 7).

Example 3.7: VEPEP-3 Mediated Delivery of Small Hydrophobic Molecules in Different Cell Lines VEPEP-3 peptides have been used for the delivery of different small fluorescent hydrophobic and charged molecules as well as doxorubicin/porphyrin/taxol on different cell lines, including primary cell lines and challenging cell lines. VEPEP-3 peptides form stable particles with small aromatic molecules including doxorubicin or fluorescent dyes. The dissociation constant for small hydrophobic molecules ranges between 0.01 to 2 µM, depending on the nature of the dyes and of the peptides.

Effect of VEPEP-3a, VEPEP-3c and VEPEP-3g mediated delivery of doxorubicin, porphyrin or taxol have been investigated on cancer cell viability. Dose-response experiments performed on cultured cells revealed that VEPEP-3 peptide mediated delivery of doxorubicin and porphyrin induced a biological response associated to cell cycle arrest and decrease in viability of MCF-7 and SCK-3-HEK2 cancer cells (FIG. 8 shows the results obtained with MCF-7 cells). The impact of carrier peptides to improve cellular uptake of small molecule drugs was estimated by following inhibition of proliferation of cancer cells.

IC50 are reported in table 4. IC50 of 0.4 µM and 10 µM were obtained for VEPEP-3/Doxo and free Doxo, respectively. Data demonstrated that Doxo is 25 fold more efficient when complexed with VEPEP-3.

TABLE 4

| Drug | VEPEP-3a 1/20 IC50 (µM) | Free drug IC50 (µM) | VEPEP-3c 1/20 IC50 (µM) | VEPEP-3g 1/20 IC50 (µM) |
| --- | --- | --- | --- | --- |
| Doxo (SKB3) | 0.3 | 10 | 0.4 | 0.2 |
| Doxo (MCF7) | 0.2 | 7 | 0.5 | 0.2 |
| Porphyrin (MCF7) | 0.8 | 25 | 1.7 | 0.5 |
| Porphyrin (SKB3) | 1.5 | 17 | 2.4 | 1.2 |

TABLE 4-continued

| Drug | VEPEP-3a 1/20 IC50 (µM) | Free drug IC50 (µM) | VEPEP-3c 1/20 IC50 (µM) | VEPEP-3g 1/20 IC50 (µM) |
| --- | --- | --- | --- | --- |
| Taxol (MCF7) | 0.2 | 7 | 0.5 | 0.7 |
| Taxol (SKB3) | 0.5 | 9 | 0.9 | 0.8 |

Example 4: NANOPEP-3 Formulations and Applications for In Vivo Delivery

NANOPEP particles contain a "peptide-core" or "core shell" corresponding to the association of either VEPEP-3 peptide or any other peptide forming non covalent complexes with its respective cargo, that is surrounded by additional VEPEP-3 "peripheral" peptides stabilizing the particle and favouring cell membrane association. The efficiency of NANOPEP is mainly controlled by the size and the charge of the particles, which should be ranging between 100-200 nm and +5-+20 Volts, respectively. Several combinations can be used for the "core" and peripheral VEPEP-3 can be functionalized or not. The choice of the peptides in the "core" is dependent on the nature of the cargoes and can be either VEPEP-6, a peptide of another VEPEP family (VEPEP-9, ... ), CADY (Crombez et al, 2009a [10]), MPG (Crombez et al, 2009b [11]) or PEP-1 (Chariot: Morris et al, 2001 [8]), etc.

The NANOPEP particles are formed in a two step process (FIG. 9): first the "core" at molar ratio of 1/5 or 1/10, then the "peripheral" at molar ratio of 1/20 up to 1/80. The multilayer organization of the particle allows their oriented functionalization, that will be chosen depending on the nature of the cellular target/tissue and administration mode.

A three step protocol (FIG. 9) has been established when particle functionalization takes place via the nitrilotriacetic acid (NTA) linked to the VEPEP-3. NTA-group is well known as being able to chelate metal and to strongly interact with histidine-tagged proteins. Coating of the particles with NTA-functionalized VEPEP-3 allows the attachment any protein harboring a histidine tag to the particle. This strategy offers the major advantage of having a common 2 layers particles "NANOPEPHIS" that can be associated to any His-tagged protein. The NANOPEPHIS strategy has been used to coat the particles with specific antibodies targeting cell surface antigen (EGF, HER-2 or MUC1) or nanobodies selected by phage display against specific cell lines for targeted delivery of peptide. NANOPEPHIS-3 strategy can be universally applied to any peptides and proteins harbouring a Histidine cluster in their sequence.

Example 5: NANOPEP-3 Strategy Applications

NANOPEP-3 strategy has been used for in vivo delivery and targeting of different cargos and different peptide-based nanoparticles. Different examples of NANOPEP-3 applications are reported hereafter.

Example 5.1: NANOPEP-3 Mediated Short Peptide In Vivo Targeted Delivery after Systemic Intravenous or Topical Injections The therapeutic potential of the NANOPEP-3 technology has been validated in vivo with peptides targeting either CDK2/CYCLIN A/E and CDK4/CYCLIN D, essential protein kinases required for the control of cell cycle progression in G1 and G2 and established therapeutic target in several cancers. The potency of this technology has been validated in vivo with peptides targeting interactions between protein kinases and their cyclin regulators, required for entry and progression through mitosis. The inventors demonstrated that combining peptide C4 or C2 with NANOPEP prevents lung and prostate tumour growth in xenografted mouse models, upon injection every three days of NANOPEP-3/C4 and NANOPEP-3/C2 at 1 mg/kg (FIG. 10). The "core" shell of the particles was formed using VEVEP-3a or VEPEP-3f peptide at a molar ratio of 20/1 or 40/1 with a C4 or C2 peptide. VEPEP-3 peptides were solubilised in water and stock solution of peptide was sonicated for 10 minutes in a water bath before complex formation. Then VEPEP-3/peptide complexes were formed by adding peptide (C2 or C4) into the peptide solution and incubating at 37° C. for 20-30 minutes to allow the carrier peptide/peptide complexes to form. Then the particles were coated with either VEPEP-3a (NANO-3A) or VEPEP-3f (NANO-3F) peptides depending on the in vivo target. The coating was performed by adding the coating peptide at a molar ratio (peptide/peptide) of 1/5 and then incubating for 20 minutes at 37° C. for obtaining stable complexes as shown in FIG. 9. The stock solutions of particles are performed in water and stable for at least three weeks at 4° C. Particles can be lyophilized for long time storage; in that case, 5 to 20% of glucose or manitol are added to the particle solution before lyophilization to stabilize the particles during the process. Before administration the particles are diluted in physiological conditions, in the presence: 0.9% NaCl and 5 to 20% glucose or manitol.

NANOPEP-3/C4 and NANOPEP-3/C2 Delivery Upon Topical and Systemic Injection

The potential of NANOPEP-3 to deliver C2 or C4 peptide in vivo was first evaluated on human prostate carcinoma cell PC3-xenografted mice (FIG. 10). The effect of local intratumoral and intravenous administration of NANOPEP-3/C4 or NANOPEP-3/C2 particles (molar ratio 20/1) on the growth of established subcutaneous tumours was evaluated. At day 50, tumor sizes in the control cohort, injected with PBS had increased by about 4.1 fold. Upon local intratumoral treatment, reductions of tumor growth by 75% and 80% were observed using 100 μg (0.5 mg/kg) of C4/NANO-PEP-3a or 3f and C2/NANOPEP-3a or 3f tumour growth was completely prevented with 500 μg (1 mg/kg) C2/NANOPEP-3a or 3f & C4/NANOPEP-3a or 3f, respectively (FIG. 10). Following systemic intravenous administration, reductions of tumor growth by 45% and 47% were observed using 500 μg (1 mg/kg) of C4/NANOPEP-3 and C2/NANOPEP-3, respectively. In both cases, inhibition of tumour growth was C4 or C2 sequence-specific, since scrambled peptide C4S complexed with NANOPEP-3 and injected into mice at 2 mg/kg was unable to inhibit tumour growth. The results demonstrated that NANOPEP-3 particles are less efficient via systemic injection, which is probably due to lower stability in the blood of the particle (see below).

NANOPEP-3 Mediated C2 and C4 Peptide Delivery Upon Systemic Injection

The stability of drug-carrier formulations in vivo and in the blood circulation is a major issue for systemic administration of therapeutics. In order to improve the bioavailability and stability of the NANOPEP-3a/peptide particles, these were coated with PEG-VEPEP-3a, thereby rendering them more suitable for systemic administration; the surface layer of NANOPEP-3 particles was functionalized with a PEG-moiety at the N-terminus of VEPEP-3 (PEG-VEPEP-3a), through activation of the N-terminal beta alanine amino group. PEGylated-NANOPEP-3a/C4 particles were obtained stepwise by complexing VEPEP-3 molecules with C4 at a molar ratio of 15/1, followed by coating of particles with a second layer of PEG-VEPEP3a at ratio 1/10. In order to analyze if increase in the distribution of C4 peptide associated to functionalized-NANOPEP-3a particles directly affects its potency to inhibit tumour growth, the particles were used for systemic intravenous administration into SKB3-HEK2 xenografted tumor mouse model. 100 μg (0.5 mg/kg) of C4 peptide complexed with PEG-NANO-PEP-3 at a 1/30 ratio were injected intravenously every three days into mice bearing SKB3-HEK2 xenografted tumor and a significant reduction in tumor size of 90% was observed at day 50 (FIG. 11), which is 10-fold more potent than the non functionalized-NANOPEP-3 nanoparticle, suggesting that PEG-increases the biodistribution of peptide in the tumour by maintaining peptide in the plasma and by stabilizing the NANOPEP-3 particle.

Example 5.2: NANOPEP-3 Mediated Anti Cyclin B1 PNA Antisens Delivery Upon Systemic Injection NANOPEP-3 was used for the delivery of antisense PNA targeting cyclin B1 antisense in vivo. NANOPEP-3H/PNA, NANOPEP-3A/PNA free or coated with PEG-VEPEP-3A particles were evaluated directly on the potency to inhibit tumour growth; the particles were used for systemic intravenous administration into SKB3-HEK2 xenografted tumor mouse model. In the later, the surface layer of NANOPEP-3 particles was functionalized with a PEG-moiety at the N-terminus of VEPEP-3A (PEG-VEPEP-3a), through activation of the N-terminal beta alanine amino group. PEGylated-NANOPEP-3/PNA particles were obtained stepwise by complexing VEPEP-3 molecules with PNA at a molar ratio of 10/1, followed by coating of particles with a second layer of PEG-VEPEP3 at ratio 1/10. 5 μg (0.1 mg/kg) and 10 μg of PNA complexed with NANOPEP-3 and PEG-NANO-PEP-3 at a 1/30 ratio were injected intravenously every three days into mice bearing SKB3-HEK2 xenografted tumor. As reported in FIG. 12, at day 50, reductions of tumor growth by 20 and 43% were obtained with 5 μg and 10 μg of PNA complexed with NANOPEP-3, respectively. A significant reduction in tumor size of 90% was observed with 5 μg of PNA complexed with PEG-NANOPEP-3, at day 50 (FIG. 12). Inhibition of tumour growth was PNA cyclin B1 sequence-specific as 50 μg scrambled PNA complexed with NANOPEP-3 and injected into mice was unable to inhibit tumour growth. These results suggested that VEPEP-3 constitutes a great carrier for in vivo delivery of PNA and that PEG-increases the biodistribution of PNA in the tumour by improving the stability of the NANOPEP-3 particle.

Example 5.3: NANOPEP-3-Mediated In Vivo Brain Targeting of Peptide

VEPEP-3 peptides were used to promote brain targeting of peptide-based nanoparticles. VEPEP-3 was used as carrier and coated with VEPEP-3 for brain targeting. VEPEP-3 peptide was also added as a coating peptide on other peptide-based nanoparticle cargo complexes (including other VEPEP family, CADY, PEP, or MPG/peptide "core shell particles"). The cargos used were either a fluorescently-labelled peptide or siRNA. Particles were formed as reported in FIG. 9. In all the cases, 5 μg of cargoes complexed with peptide carrier were injected intravenously. Then the in vivo biodistribution of the cargos was monitored using live fluorescence animal imaging. VEPEP-3/peptide results in a large accumulation of Peptide in the brain (FIG. 13), and the presence of VEPEP-3 coating induced an increase of the cargoes (peptide or siRNA) delivery into the brain. Monitoring fluorescence of labelled cargoes showed a 5 to 10-fold increase in the brain, in comparison to control experiments in the absence of VEPEP-3 coating of the particle. The presence of VEPEP-3 coating also increased by a 3-fold factor the knockdown of GAPDH in the brain (FIG. 13). Taken together, these results demonstrated that VEPEP-3 peptide improves significantly brain targeting of peptide-based nanoparticles and can be used for brain targeting either as a carrier or as a coating layer of already formed peptide-based nanoparticles.

Example 5.4: NANOPEP-3 Mediated In Vivo Delivery of Cargo Via Different Administration Routes NANOPEP-3 based particles have been evaluated using different administration routes including systemic intravenous, intrarectal, intranasal and transdermal administrations. A fluorescently labelled peptide or protein (small nanobody) with Alexa 700 was complexed into NANOPEP-3 particles. Biodistribution of the fluorescently labelled peptide/protein was evaluated in vivo on Balb6 Mouse, 5 hr after a single administration of 10 µg peptide or protein in NANOPEP-3 particles. Intravenous and intrarectal administrations of the NANOPEP-3/peptide or NANOPEP-3/protein complex allowed the delivery of the peptide in most of the analyzed tissues, with a significant delivery in the brain and ganglions (FIGS. 14 A-B). For protein, the delivery was mainly in lung, liver, kidney, brain and lymphe node. Intranasal and intratracheal administrations allowed the delivery of peptide mainly into the brain, lung, liver, pancreas and kidney and protein into the lung, liver and brain. Finally, transdermal administration is limited to the delivery of the peptide and protein into and through the skin and muscles, but not in the other tissues (FIGS. 14 C-D).

REFERENCES

[1] D J. Glover, H J. Lipps, D A. Jans, Towards safe, non-viral therapeutic gene expression in humans Nat. Rev. Genet. 6 (2005) 299-310

[2] K A. Whitehead, R. Langer, D G. Anderson, Knocking down barriers: advances in siRNA delivery. Nat Rev Drug Discov. 8 (2009) 129-138.

[3] U Langel, Handbook of Cell-Penetrating Peptides: (Eds.: U. Langel) CRC Taylor & Francis, Boca Raton (2007).

[4] F. Heitz, M C. Morris, G. Divita, Twenty years of cell-penetrating peptides: from molecular mechanisms to therapeutics; British Journal of Pharmacology 157 (2009) 195-206.

[5] S. Deshayes, M C Morris, F. Heitz, G. Divita. Delivery of proteins and nucleic acids using a non-covalent peptide-based strategy. Adv Drug Deliv Rev. 60 (2008) 537-547.

[6] S. Deshayes, M C. Morris, G. Divita, F. Heitz Cell-penetrating peptides: tools for intracellular delivery of therapeutics, Cell Mol Life Sci. 62 (2005) 1839-1849.

[7] M C. Morris, P. Vidal, L. Chaloin, F. Heitz, G Divita A new peptide vector for efficient delivery of oligonucleotides into mammalian cells, Nucleic Acids Res. 25 (1997) 2730-2736.

[8] M C. Morris, J. Depollier, J. Mery, F. Heitz, G. Divita A peptide carrier for the delivery of biologically active proteins into mammalian cells, Nat. Biotechnol. 19 (2001) 1173-1176.

[9] Mery J, Brugidou J, Derancourt J. Disulfide bond as peptide-resin linkage in Boc-Bzl SPPS, for potential biochemical applications, Pept Res. 1992 July-August; 5(4):233-40.

[10] L. Crombez, M. C. Morris, S. Dufort, G. Aldrian-Herrada, Q. Nguyen, G. Mc Master, J. L. Coll, F. Heitz, G. Divita, Targeting cyclin B1 through peptide-based delivery of siRNA prevents tumour growth, Nucleic Acids Res. 37 (2009) 4559-4569.

[11] L. Crombez, G. Aldrian-Herrada, K. Konate, Q. N. Nguyen, G. K. McMaster, R. Brasseur, F. Heitz, G. Divita, A new potent secondary amphipathic cell-penetrating peptide for siRNA delivery into mammalian cells, Mol. Ther. 17 (2009) 95-103.

[12] Verdine, G. L. and Hilinski, G. J. (2012), Stapled peptides for intracellular drug targets. Methods in Enzymology, vol 503, p 3-33.

The invention claimed is:

1. A complex comprising:
   a) a cell-penetrating peptide characterized in that it comprises an amino acid sequence selected from the group consisting of SEQ ID NOs: 1-4; and
   b) a cargo selected from the group consisting of peptides, proteins, peptide analogs, uncharged oligonucleotides, PNAs and small hydrophobic molecules.

2. The complex of claim 1, wherein the cell-penetrating peptide further comprises a) an acetyl group or a polyethylene glycol covalently linked to the N-terminal end of the amino acid sequence, and/or b) a cysteamide group covalently linked to the C-terminal end of the amino acid sequence.

3. The complex of claim 1, wherein the cargo is a peptide, protein, or PNA.

4. A nanoparticle comprising a core comprising a cargo selected from the group consisting of peptides, proteins, peptide analogs, uncharged oligonucleotides, PNAs and small hydrophobic molecules, wherein:
   a) the core comprises the cargo complexed to a VEPEP-3 cell-penetrating peptide comprising an amino acid sequence selected from the group consisting of SEQ ID NOs: 1-4, and the core is coated by a peripheral cell-penetrating peptide; or b) the core comprises the cargo complexed to a first entity selected from the group consisting of cell-penetrating peptides, liposomes, polycationic structures and carbon nanoparticles, and the core is coated by a peripheral cell-penetrating peptide that is a VEPEP-3 cell-penetrating peptide comprising an amino acid sequence selected from the group consisting of SEQ ID NOs: 1-4.

5. The nanoparticle of claim 4, wherein the first entity is a cell-penetrating peptide selected from the group consisting of VEPEP-6a (SEQ ID No: 29), VEPEP-6b (SEQ ID No: 30), VEPEP-6c (SEQ ID No: 31), VEPEP-6d (SEQ ID No: 32), VEPEP-6e (SEQ ID No: 33), VEPEP-6f (SEQ ID No: 34), VEPEP-9a1 (SEQ ID No: 35), VEPEP-9a2 (SEQ ID No: 36), VEPEP-9b1 (SEQ ID No: 37), VEPEP-9b2 (SEQ ID No: 38), VEPEP-9c1 (SEQ ID No: 39), VEPEP-9c2 (SEQ ID No: 40), CADY, MPG, PEP-1, PPTG 1, and poly Arginine.

6. The nanoparticle of claim 4, wherein the VEPEP-3 cell-penetrating peptide further comprises a) an acetyl group or a poly-ethylene glycol covalently linked to the N-terminal end of the amino acid sequence, and/or b) a cysteamide group covalently linked to the C-terminal end of the amino acid sequence.

7. A method for delivering a molecule into a cell in vitro, comprising contacting the cell with the complex of claim 1, wherein the cargo of the complex comprises the molecule.

8. A method for delivering a molecule into a cell in vitro, comprising contacting the cell with the nanoparticle of claim 4, wherein the cargo of the nanoparticle comprises the molecule.

9. A complex comprising:
a) a cell-penetrating peptide characterized in that it comprises an amino acid sequence selected from the group consisting of SEQ ID NOs: 5-8; and
b) a cargo selected from the group consisting of peptides, proteins, peptide analogs, uncharged oligonucleotides, PNAs and small hydrophobic molecules.

10. The complex of claim 9, wherein the cell-penetrating peptide further comprises a) an acetyl group or a poly-ethylene glycol covalently linked to the N-terminal end of the amino acid sequence, and/or b) a cysteamide group covalently linked to the C-terminal end of the amino acid sequence.

11. The complex of claim 9, wherein the cargo is protein.

12. A nanoparticle comprising a core comprising a cargo selected from the group consisting of peptides, proteins, peptide analogs, uncharged oligonucleotides, PNAs and small hydrophobic molecules, wherein:
a) the core comprises the cargo complexed to a VEPEP-3 cell-penetrating peptide comprising an amino acid sequence selected from the group consisting of SEQ ID NOs: 5-8, and the core is coated by a peripheral cell-penetrating peptide; or
b) the core comprises the cargo complexed to a first entity selected from the group consisting of cell-penetrating peptides, liposomes, polycationic structures and carbon nanoparticles, and the core is coated by a peripheral cell-penetrating peptide that is a VEPEP-3 cell-penetrating peptide comprising an amino acid sequence selected from the group consisting of SEQ ID NOs: 5-8.

13. The nanoparticle of claim 12, wherein the first entity is a cell-penetrating peptide selected from the group consisting of VEPEP-6a (SEQ ID No: 29), VEPEP-6b (SEQ ID No: 30), VEPEP-6c (SEQ ID No: 31), VEPEP-6d (SEQ ID No: 32), VEPEP-6e (SEQ ID No: 33), VEPEP-6f (SEQ ID No: 34), VEPEP-9a1 (SEQ ID No: 35), VEPEP-9a2 (SEQ ID No: 36), VEPEP-9b1 (SEQ ID No: 37), VEPEP-9b2 (SEQ ID No: 38), VEPEP-9c1 (SEQ ID No: 39), VEPEP-9c2 (SEQ ID No: 40), CADY, MPG, PEP-1, PPTG 1, and poly Arginine.

14. The nanoparticle of claim 12, wherein the VEPEP-3 cell-penetrating peptide further comprises a) an acetyl group or a poly-ethylene glycol covalently linked to the N-terminal end of the amino acid sequence, and/or b) a cysteamide group covalently linked to the C-terminal end of the amino acid sequence.

15. A method for delivering a molecule into a cell in vitro, comprising contacting the cell with the complex of claim 9, wherein the cargo of the complex comprises the molecule.

16. A method for delivering a molecule into a cell in vitro, comprising contacting the cell with the nanoparticle of claim 12, wherein the cargo of the nanoparticle comprises the molecule.

17. A method of treating a disease in an individual, comprising administering to the individual an effective amount of a therapeutic composition comprising a VEPEP-3 cell-penetrating peptide and a cargo selected from the group consisting of peptides, proteins, peptide analogs, uncharged oligonucleotides, PNAs and small hydrophobic molecules, wherein the VEPEP-3 cell-penetrating peptide comprises an amino acid sequence selected from the group consisting of SEQ ID NOs: 1-8, wherein the disease is a brain disease or a lymph node disease.

18. The method of claim 17, wherein the therapeutic composition comprises nanoparticles comprising a core comprising the cargo, and wherein:
a) the core comprises the cargo complexed to the VEPEP-3 cell-penetrating peptide, and the core is coated by a peripheral cell-penetrating peptide; or
b) the core comprises the cargo complexed to a first entity selected from the group consisting of cell-penetrating peptides, liposomes, polycationic structures and carbon nanoparticles, and the core is coated by a peripheral cell-penetrating peptide that is the VEPEP-3 cell-penetrating peptide.

19. The method of claim 17, wherein the VEPEP-3 cell-penetrating peptide comprises the amino acid sequence of SEQ ID NO: 1 or 2.

20. The method of claim 17, wherein the VEPEP-3 cell-penetrating peptide comprises the amino acid sequence of SEQ ID NO: 6 or 7.

* * * * *